United States Patent
Ameer et al.

(10) Patent No.: US 10,406,385 B2
(45) Date of Patent: Sep. 10, 2019

(54) PHOTOLUMINESCENT PANTHENOL CITRATE BIOMATERIALS

(71) Applicant: Northwestern University, Evanston, IL (US)

(72) Inventors: Guillermo A. Ameer, Chicago, IL (US); Robert van Lith, Evanston, IL (US); Jian Yang, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/536,858

(22) PCT Filed: Dec. 18, 2015

(86) PCT No.: PCT/US2015/066723
§ 371 (c)(1),
(2) Date: Jun. 16, 2017

(87) PCT Pub. No.: WO2016/100842
PCT Pub. Date: Jun. 23, 2016

(65) Prior Publication Data
US 2017/0368377 A1 Dec. 28, 2017

Related U.S. Application Data

(60) Provisional application No. 62/094,482, filed on Dec. 19, 2014.

(51) Int. Cl.
| | |
|---|---|
| *A61K 8/49* | (2006.01) |
| *A61K 8/85* | (2006.01) |
| *A61L 27/50* | (2006.01) |
| *A61Q 17/04* | (2006.01) |
| *C08G 69/44* | (2006.01) |
| *A61K 31/787* | (2006.01) |
| *A61K 31/5365* | (2006.01) |
| *G02B 1/04* | (2006.01) |
| *C08G 69/40* | (2006.01) |

(52) U.S. Cl.
CPC ............ *A61Q 17/04* (2013.01); *A61K 8/49* (2013.01); *A61K 8/85* (2013.01); *A61K 31/5365* (2013.01); *A61K 31/787* (2013.01); *A61L 27/50* (2013.01); *C08G 69/44* (2013.01); *G02B 1/043* (2013.01); *A61L 2430/16* (2013.01); *C08G 69/40* (2013.01)

(58) Field of Classification Search
None
See application file for complete search history.

(56) References Cited

U.S. PATENT DOCUMENTS

| | | |
|---|---|---|
| 7,026,360 B1 | 4/2006 | Festo |
| 8,568,765 B2 | 10/2013 | Ameer et al. |
| 8,580,912 B2 | 11/2013 | Ameer et al. |
| 8,758,796 B2 | 6/2014 | Ameer et al. |
| 8,772,437 B2 | 7/2014 | Ameer et al. |
| 8,871,717 B2 | 10/2014 | Osborne |
| 2007/0213409 A1 | 9/2007 | Breitenbach et al. |
| 2008/0019921 A1* | 1/2008 | Zhang ............... A61K 49/0004 424/9.6 |
| 2014/0037588 A1 | 2/2014 | Yang et al. |
| 2014/0135407 A1 | 5/2014 | Ameer et al. |
| 2014/0155516 A1 | 6/2014 | Ameer et al. |
| 2014/0243423 A1 | 8/2014 | Gurge et al. |

OTHER PUBLICATIONS

Arshady, Preparation of biodegradable microspheres and microcapsules: 2. Polyactides and related plyesters. J. Controlled Release 1991;17:1-22.
Holland et al., Polymers for biodegradeable medical devices. 1. The potential of polyesters as controlled macromolecular release systems, Journal of Controlled Release, 4 (1986) 155-180.
Illum et al., "Polymers in Controlled Drug Delivery" Wright, Bristol, 1987. TOC Only.
Pitt, The controlled parenteral delivery of polypeptides and proteins. Int. J. Phar. 1990;59:173-196.
Beasley et al., Characterization of the UVA protection provided by avobenzone, zinc oxide, and titanium dioxide in broad-spectrum sunscreen products, Am J Clin Dermatol. Dec. 1, 2010;11(6):413-21.
Combs, The vitamins: fundamental aspects in nutrition and health, Pantothenic Acid. 2012: p. 339-348.
Ebner et al., Topical Use of Dexpanthenol in Skin Disorders, Am J Clin Dermatol. 2002;3(6):427-33.
Gonzalez et al., The latest on skin photoprotection, Clin Dermatol. Nov.-Dec. 2008;26(6):614-26.
Magro et al., The application of a monoclonal antibody to CD62L on paraffin-embedded tissue samples in the assessment of the cutaneous T-cell infiltrates, J Cutan Pathol. Jan. 2005;32(1):12-20.
Kasprzyk et al., Novel efficient fluorophores synthesized from citric acid, RSC Adv. 2012.
Sambandan et al., Sunscreens: an overview and update, J Am Acad Dermatol. Apr. 2011;64(4):748-58.
Seite et al., A full-UV spectrum absorbing daily use cream protects human skin against biological changes occurring in photoaging, Photodermatol Photoimmunol Photomed. Aug. 2000;16(4):147-55.

(Continued)

*Primary Examiner* — Katherine Peebles

(74) *Attorney, Agent, or Firm* — Casimir Jones SC; David W. Staple

(57) ABSTRACT

Provided herein are compositions comprising panthenol-citrate containing materials. In particular, panthenol citrate compounds, oligomers, and polymers, and methods of use and synthesis thereof, are provided herein. Panthenol-citrate containing materials are a class of nontoxic, photoluminescent-chromophore-containing compounds, oligomers, and polymers with high absorption in the UVA and UVB range that can be incorporated and/or engineered into a variety of optically-active biomaterials (e.g., sunscreen products).

7 Claims, 27 Drawing Sheets

(56) References Cited

OTHER PUBLICATIONS

Serrano et al., Novel biodegradable shape-memory elastomers with drug-releasing capabilities, Adv Mater. May 17, 2011;23(19):2211-5.
Spry et al., Pantothenamides are Potent, On-Target Inhibitors of Plasmodium falciparum Growth When Serum Pantetheinase Is Inactivated, PLoS One. 2013;8(2):e54974.
Van Lith et al., Engineering biodegradable polyester elastomers with antioxidant properties to attenuate oxidative stress in tissues, Biomaterials. Sep. 2014;35(28):8113-22.
Wiederholt et al., Calcium pantothenate modulates gene expression in proliferating human dermal fibroblasts, Exp Dermatol. Nov. 2009;18(11):969-78.
Yang et al., A thermoresponsive biodegradable polymer with intrinsic antioxidant properties, Biomacromolecules. Nov. 10, 2014;15(11):3942-52.
Yang et al., Development of aliphatic biodegradable photoluminescent polymers, Proc Natl Acad Sci U S A. Jun. 23, 2009;106(25):10086-91.
Yang et al., Synthesis and evaluation of poly(diol citrate) biodegradable elastomers, Biomaterials. Mar. 2006;27(9):1889-98.
Zanatta et al., Photoprotective potential of emulsions formulated with Buriti oil (*Mauritia flexuosa*) against UV irradiation on keratinocytes and fibroblasts cell lines, Food Chem Toxicol. Jan. 2010;48(1):70-5.
International Search Report of related PCTUS2015066723, dated Feb. 25, 2016, 8 pages.

* cited by examiner a)

b)

c)

d)

(a)

(b)

(b)

Fluorescent emission and heat absorption:
$S_1 = S_0 + h\nu + \text{Heat}$ (c)

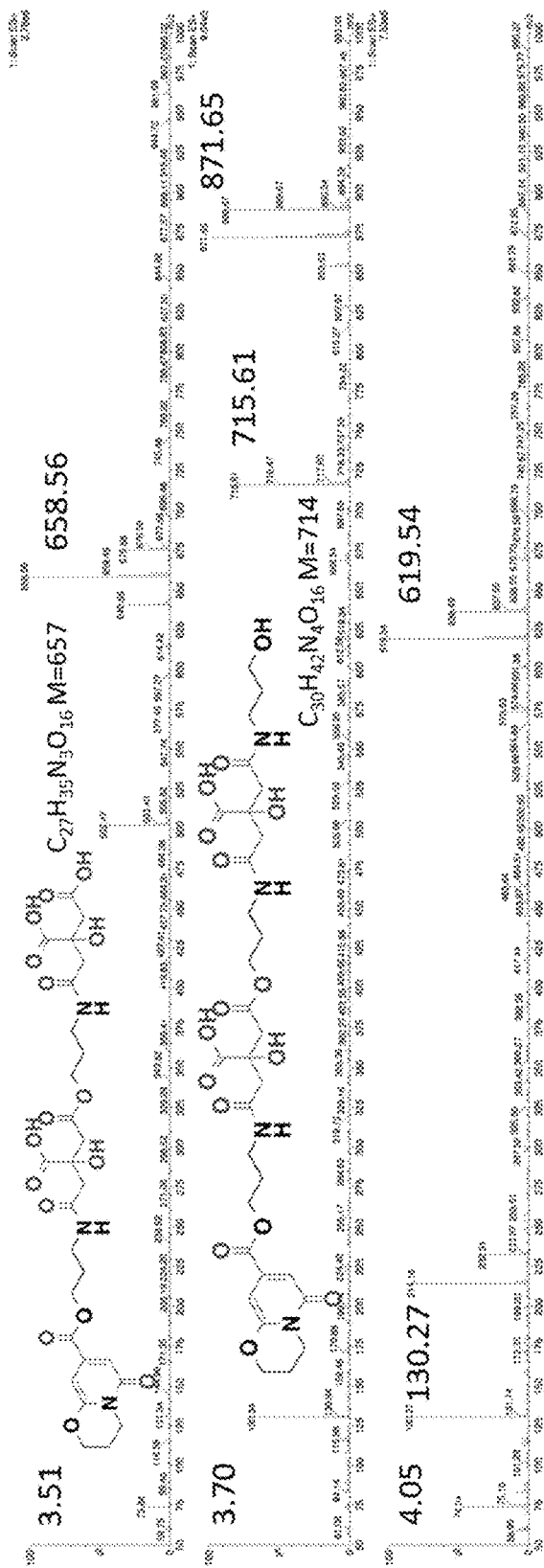

PHOTOLUMINESCENT PANTHENOL CITRATE BIOMATERIALS

CROSS-REFERENCE TO RELATED APPLICATIONS

The present invention claims the priority benefit of U.S. Provisional Patent Application 62/094,482, filed Dec. 19, 2014, which is incorporated by reference in its entirety.

FIELD

Provided herein are compositions comprising panthenol-citrate containing materials. In particular, panthenol citrate compounds, oligomers, and polymers, and methods of use and synthesis thereof, are provided herein.

BACKGROUND

Skin is the first barrier to environmental exposures such as ultraviolet radiation, which is divided into UVC radiation (200-280 nm), UVB radiation (280-320 nm) and UVA radiation (320-400 nm). Compared to UVC radiation, which is predominately filtered by the ozone layer, UVB radiation is mainly absorbed by the epidermis and can induce skin cancers in animals due to DNA damage (Hussein. J Cutan Pathol, 2005. 32: p. 15; herein incorporated by reference in its entirety). UVA radiation can penetrate through dermis to subcutaneous tissues and induce various biological responses, ranging from erythema to photoaging (Zanatta et al. Food and Chemical Toxicology, 2010. 48(1): p. 70-75; herein incorporated by reference in its entirety). It is now recognized that both UVA and UVB wavelengths, received during daily exposure to sun, contribute to chronic photodamage of human skin (Gonzalez et al. Clin Dermatol, 2008. 26(6): p. 614-26; herein incorporated by reference in its entirety). Adequate protection against solar UV exposure can prevent cellular and molecular changes that lead to photoaging, photoimmunosuppression and photocarcinogenesis (Seite. Photodermatology Photoimmunology Photomedicine, 2000. 16; herein incorporated by reference in its entirety).

There are 17 active sunscreen ingredients currently approved by the FDA, including various organic and inorganic compounds that are used as filters to help prevent skin damage. Some of these compounds may have adverse effects such as contact sensitivity, increased risk of vitamin D deficiency, and estrogenicity (Sambandan & Ratner. J Am Acad Dermatol, 2011. 64(4): p. 748-58; herein incorporated by reference in its entirety). Organic chemicals, such as avobenzone, are strong absorbers; whereas, inorganic compounds, such as zinc or titanium oxides, use scattering and absorption mechanisms for protection. Although zinc oxide is the most efficient at protecting against both UVA and UVB radiation, products that use this ingredient leave an undesirable opaque and often dense film on the skin, making their proper use uncomfortable due to increased retained body heat and cosmetically unpleasing. This problem is more prominent for people with darker shades of skin color. Although nanoparticle versions of the metal oxides appear to have better skin application and spreading properties, they only marginally improve the aesthetically unpleasing effect when used on skin and the safety and fate of the nanoparticles in the human body remain a concern (Sambandan & Ratner. J Am Acad Dermatol, 2011. 64(4): p. 748-58; herein incorporated by reference in its entirety). The use of avobenzone eliminates the consistency and aesthetic problems encountered with metal oxides, but sunscreen formulations that use it require chemical photostabilizers in order for the protective absorption spectra to be maintained for a 2 to 3-hour duration (Gonzalez et al. Clin Dermatol, 2008. 26(6): p. 614-26; herein incorporated by reference in its entirety). The efficacy of avobenzone is also very sensitive to the ingredients used in the sunscreen formulation (Beasley. Am J Clin Dermatol, 2010. 11(6): p. 10; herein incorporated by reference in its entirety). As for other small molecular UV absorbers such as aminobenzoates and benzophenones for topical application, their safety remains a concern (Gonzalez et al. Clin Dermatol, 2008. 26(6): p. 614-26; herein incorporated by reference in its entirety). Hence, there is a need for new materials that protect from UVA and UVB radiation that are safe, effective, inexpensive, and can be easily formulated for a skin application that is aesthetically pleasing and therefore would be used by many more people to help curb the rising rates of skin cancer.

SUMMARY

Provided herein are compositions comprising panthenol-citrate containing materials. In particular, panthenol citrate compounds, oligomers, and polymers, and methods of use and synthesis thereof, are provided herein. Panthenol-citrate containing materials are a class of nontoxic, photoluminescent-chromophore-containing compounds, oligomers, and polymers with high absorption in the UVA and UVB range that can be incorporated and/or engineered into a variety of optically-active biomaterials (e.g., sunscreen products).

In some embodiments, provided herein are compositions (e.g., compounds, oligomers, polymers, thermosets, etc.) comprising panthenol citrate (or panthenol citric acid (PAN-CA)) and of the formula:

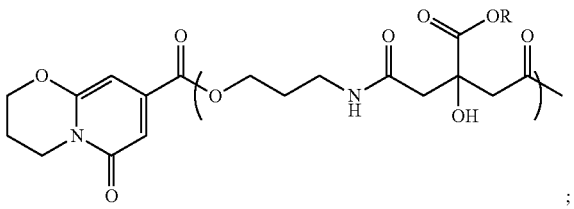

wherein R is selected from the group consisting of H, pantoic acid and β-alanol (a.k.a., 3-amino-1-propanol). In some embodiments, the panthenol citrate comprises the formula:

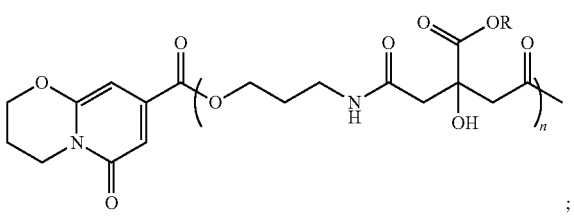

wherein n is 0 to 100 (e.g., 0, 1, 2, 3, 4, 5, 6, 7, 8, 9, 10, 20, 30, 40, 50, 100, or ranges therein); and wherein R is selected from the group consisting of H, pantoic acid and β-alanol (a.k.a., 3-amino-1-propanol). In some embodiments, the panthenol citrate is the product of the oligomerization of panthenol and citric acid. In some embodiments, the panthenol citrate is water soluble. In some embodiments, the panthenol citrate precipitates in ethanol and acetone. In some embodiments, the panthenol citrate is not a solid (e.g., at room temperature and/or atmospheric pressure). In some embodiments, the panthenol citrate is not crosslinked (e.g., not a thermoset elastomer). In some embodiments, provided herein are branched oligomers or polymers (e.g., branched but not sufficiently crosslinked to create a thermoset) of panthenol citrate. In some embodiments, provided herein are linear oligomers or polymers (e.g., substantially no branching) of panthenol citrate. In some embodiments, the panthenol citrate compounds, oligomers or polymers are water soluble.

In some embodiments, provided herein are compositions (e.g., compounds, oligomers, polymers, thermosets, etc.) comprising panthenol citrate and further comprising one or more additional monomers selected from the group consisting of: polyethylene glycol, itaconic acid, N-isopropylacrylamide, glycerol, glycerol 1,3-diglycerolate diacrylate and a linear aliphatic diol. Exemplary oligomers of panthenol citrate and other monomers are described below. These are exemplary, and should not be viewed as limiting the scope of the invention.

In some embodiments, a composition comprises panthenol citrate and polyethylene glycol (PAN-CA-PEG). In some embodiments, the composition comprises the formula:

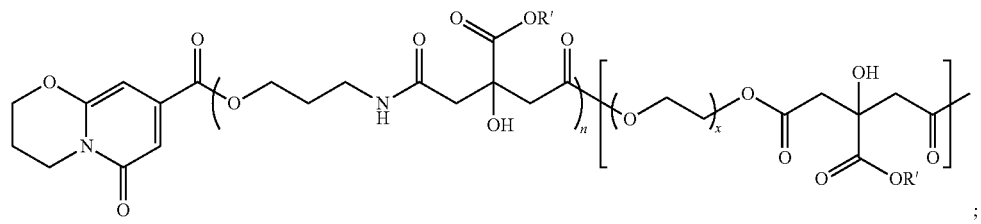

wherein n is 0 to 100 (e.g., 0, 1, 2, 3, 4, 5, 6, 7, 8, 9, 10, 20, 30, 40, 50, 100, or ranges therein), wherein x is 4-24 (e.g., 4, 6, 8, 10, 12, 14, 16, 18, 22, 24, or ranges therein), and wherein R' is selected from the group consisting of H, pantoic acid, β-alanol (a.k.a., 3-amino-1-propanol) and polyethylene glycol. In some embodiments, the composition comprises the formula:

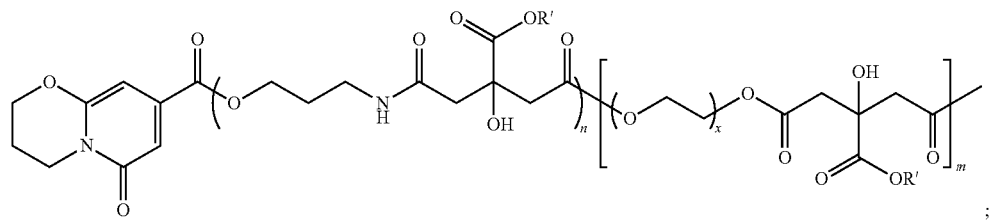

wherein n is 0 to 100 (e.g., 0, 1, 2, 3, 4, 5, 6, 7, 8, 9, 10, 20, 30, 40, 50, 100, or ranges therein) and m is 1 to 1000 (e.g., 1, 2, 3, 4, 5, 6, 7, 8, 9, 10, 20, 30, 40, 50, 100, 200, 300, 400, 500, 1000, or ranges therein); wherein x is 4-24 (e.g., 4, 6, 8, 10, 12, 14, 16, 18, 22, 24, or ranges therein), and wherein R' is selected from the group consisting of H, pantoic acid, β-alanol (a.k.a., 3-amino-1-propanol) and polyethylene glycol. In some embodiments, the composition is the product of the reaction, oligomerization, or polymerization of panthenol, citric acid, and polyethylene glycol. In some embodiments, the composition is water soluble.

In some embodiments, the composition comprises panthenol citrate and itaconic acid (PAN-CA-IA). In some embodiments, the composition comprises the formula:

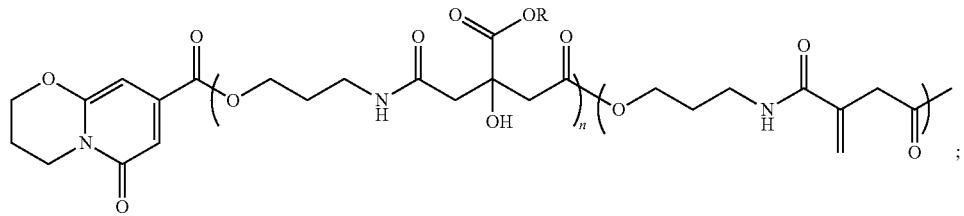

wherein n is 0 to 100 (e.g., 0, 1, 2, 3, 4, 5, 6, 7, 8, 9, 10, 20, 30, 40, 50, 100, or ranges therein), wherein R is selected from the group consisting of H, pantoic acid and β-alanol (a.k.a., 3-amino-1-propanol). In some embodiments, the composition comprises the formula:

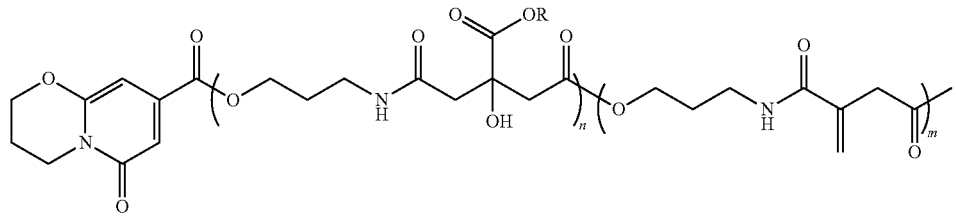

wherein n is 0 to 100 (e.g., 0, 1, 2, 3, 4, 5, 6, 7, 8, 9, 10, 20, 30, 40, 50, 100, or ranges therein) and m is 1 to 1000 (e.g., 1, 2, 3, 4, 5, 6, 7, 8, 9, 10, 20, 30, 40, 50, 100, 200, 300, 400, 500, 1000, or ranges therein), and wherein R is selected from the group consisting of H, pantoic acid and β-alanol (a.k.a., 3-amino-1-propanol). In some embodiments, the composition is the product of the reaction, oligomerization, or polymerization of panthenol, citric acid, and itaconic acid. In some embodiments, the composition is water soluble.

In some embodiments, a composition (e.g., compound, oligomer, polymer, thermoset, etc.) comprises panthenol citrate and a linear aliphatic diol (PAN-CA-AD). In some embodiments, the composition comprises the formula:

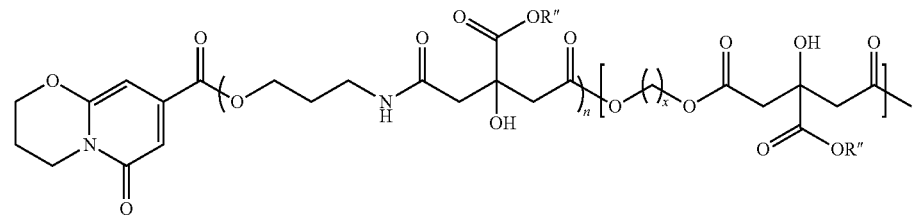

wherein n is 0 to 100 (e.g., 0, 1, 2, 3, 4, 5, 6, 7, 8, 9, 10, 20, 30, 40, 50, 100, or ranges therein), wherein x is 2-20 (e.g., 2, 3, 4, 5, 6, 7, 8, 9, 10, 11, 12, 13, 14, 15, 16, 17, 18, 19, 20, and ranges therein); wherein R" is selected from the group consisting of H, pantoic acid, β-alanol (a.k.a., 3-amino-1-propanol) and aliphatic diol. In some embodiments, the composition comprises the formula:

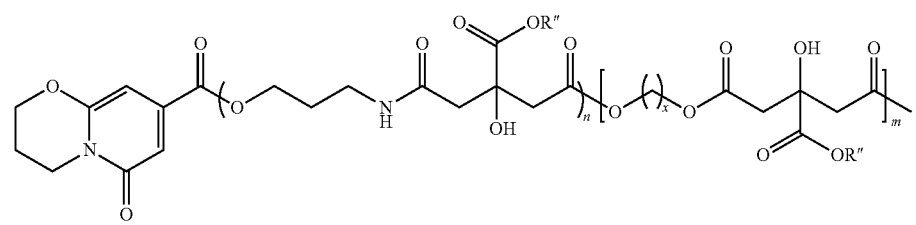

wherein n is 0 to 100 (e.g., 0, 1, 2, 3, 4, 5, 6, 7, 8, 9, 10, 20, 30, 40, 50, 100, or ranges therein) and m is 1 to 1000 (e.g., 1, 2, 3, 4, 5, 6, 7, 8, 9, 10, 20, 30, 40, 50, 100, 200, 300, 400, 500, 1000, or ranges therein); wherein x is 2-20 (e.g., 2, 3, 4, 5, 6, 7, 8, 9, 10, 11, 12, 13, 14, 15, 16, 17, 18, 19, 20, or ranges therein); wherein R" is selected from the group consisting of H, pantoic acid, β-alanol (a.k.a., 3-amino-1-propanol) and aliphatic diol. In some embodiments, the linear aliphatic diol is of the formula $HO(CH_2)_xOH$, wherein x is 2 to 20 (e.g., 2, 3, 4, 5, 6, 7, 8, 9, 10, 11, 12, 13, 14, 15, 16, 17, 18, 19, 20). In some embodiments, the linear aliphatic diol is propanediol (PAN-CA-PD), butanediol (PAN-CA-BD), hexanediol (PAN-CA-HD), octanediol (PAN-CA-OD), decanediol (PAN-CA-DD), dodecanediol (PAN-CA-DDD), hexadecanediol (PAN-CA-HDD), etc. In some embodiments, the oligomeric composition is the product of the reaction, oligomerization, or polymerization of panthenol, citric acid, and a linear aliphatic diol. In some embodiments, a composition comprises a pre-polymer or pre-oligomer (e.g., uncrosslinked) of panthenol, citric acid, and a linear aliphatic diol. In some embodiments, a pre-polymer or pre-oligomer (e.g., uncrosslinked) of panthenol, citric acid, and a linear aliphatic diol is ethanol soluble, but not water-soluble. In some embodiments, a composition comprises a thermoset polymer and/or oligomer network (e.g., extensively crosslinked) of panthenol, citric acid, and a linear aliphatic diol. In some embodiments, a composition comprising panthenol, citric acid, and a linear aliphatic diol is a solid.

In some embodiments, the composition comprises panthenol citrate, itaconic acid, polyethylene glycol, glycerol 1,3-diglycerolate diacrylate and N-isopropylacrylamide. In some embodiments, the composition comprises the formula:

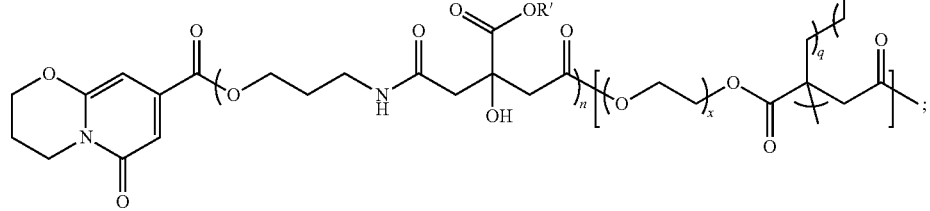

wherein x is 4 to 24 (e.g., 2, 4, 6, 8, 10, 12, 14, 16, 18, 20, 22, 24, and ranges therein); wherein n is 0 to 100 (e.g., 0, 1, 2, 3, 4, 5, 6, 7, 8, 9, 10, 20, 30, 40, 50, 100, or ranges therein), q and p is 1 to 1000 (e.g., 2, 3, 4, 5, 6, 7, 8, 9, 10, 20, 30, 40, 50, 100, 200, 300, 400, 500, 1000, or ranges therein); wherein R' is selected from the group consisting of H, pantoic acid, β-alanol (a.k.a., 3-amino-1-propanol) and polyethylene glycol. In some embodiments, the composition comprises the formula:

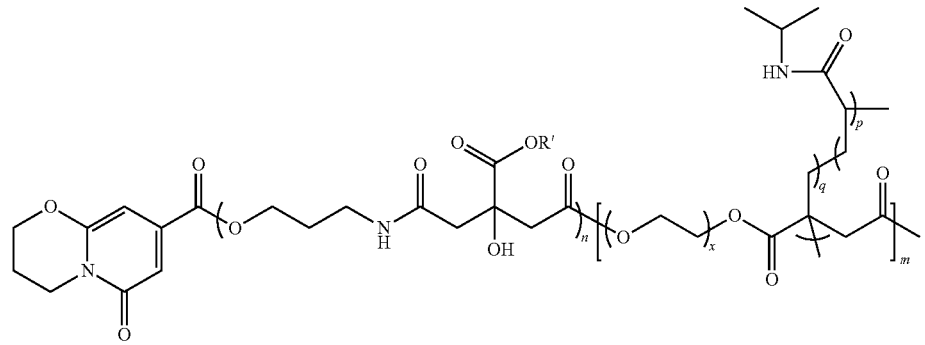

wherein n is 0 to 100 (e.g., 0, 1, 2, 3, 4, 5, 6, 7, 8, 9, 10, 20, 30, 40, 50, 100, or ranges therein), m, q and p is 1 to 1000 (e.g., 1, 2, 3, 4, 5, 6, 7, 8, 9, 10, 20, 30, 40, 50, 100, 200, 300, 400, 500, 1000, or ranges therein); wherein x is 4 to 24 (e.g., 2, 4, 6, 8, 10, 12, 14, 16, 18, 20, 22, 24, and ranges therein); wherein R' is selected from the group consisting of H, pantoic acid, β-alanol (a.k.a., 3-amino-1-propanol) and polyethylene glycol. In some embodiments, the oligomeric composition is the product of the reaction, oligomerization, or polymerization of panthenol, citric acid, itaconic acid, polyethylene glycol, glycerol 1,3-diglycerolate diacrylate and N-isopropylacrylamide.

In some embodiments, provided herein are composites of panthenol citrate oligomers (e.g., PAN-CA, PAN-CA-PEG, PAN-CA-IA, PAN-CA-AD (e.g., PAN-CA-OD), PAN-PP-CIN, etc.) and one or more additional materials (e.g., a polymeric component). In some embodiments, the additional material is a polymeric component, selected from poly(diol citrate) (e.g., butanediol, hexanediol, octanediol, decanediol, dodecanediol, hexadecanediol, etc.), poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D, L-lactide), poly(caprolactone), poly(trimethylene carbonate), polyester amide, or co-polymers or composites thereof.

In some embodiments, provided herein are compositions comprising the panthenol citrate oligomers described herein (e.g., PAN-CA, PAN-CA-PEG, PAN-CA-IA, PAN-CA-AD (e.g., PAN-CA-OD), PAN-PPCIN, etc.) and formulated for topical administration to a human or animal subject. In some embodiments, compositions for topical administration are optionally formulated as ointments, creams, suspensions, lotions, powders, solutions, pastes, gels, sprays, aerosols or oils. In some embodiments, topical formulations include a compound(s) that enhances absorption or penetration of active agent(s) through the skin or other affected areas. Examples of such dermal penetration enhancers include dimethylsulfoxide (DMSO) and related analogues. In certain embodiments, the aqueous phase of a cream base includes, for example, at least about 30% w/w of a polyhydric alcohol, e.g., an alcohol having two or more hydroxyl groups such as propylene glycol, butane-1,3-diol, mannitol, sorbitol, glycerol and polyethylene glycol and mixtures thereof. In some embodiments, oily phase emulsions are constituted from known ingredients in a known manner. This phase typically comprises an emulsifier (otherwise known as an emulgent), it is also desirable in some embodiments for this phase to further comprises a mixture of at least one emulsifier with a fat or an oil or with both a fat and an oil. In some embodiments, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations. Emulgents and emulsion stabilizers suitable for use in embodiments described herein include Tween 60, Span 80, cetostearyl alcohol, myristyl alcohol, glyceryl monostearate and sodium lauryl sulfate.

DEFINITIONS

Figure 1:
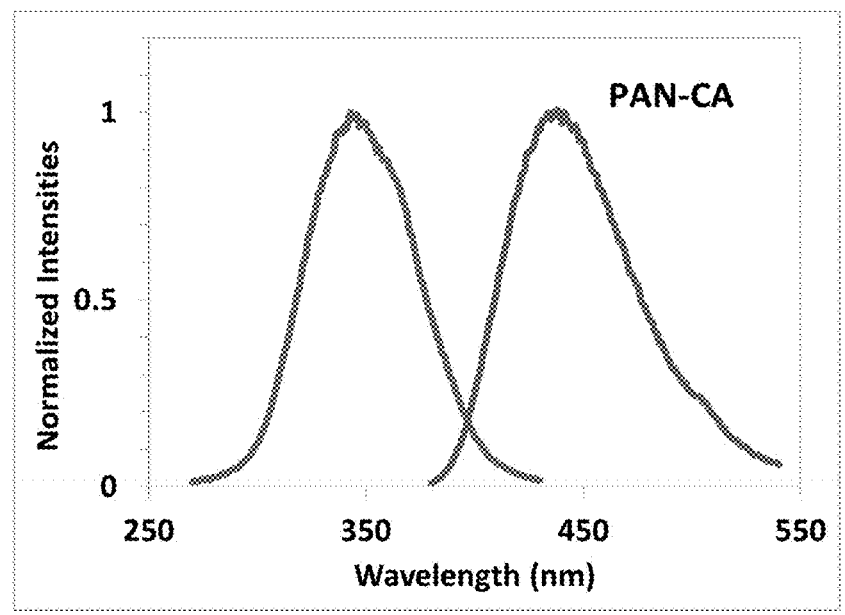
FIG. 1A-D. (a) Nomalized excitation and emission intensities of panthenol citrate (PAN-CA) in $H_2O$ of 10 mg/ml. (b) Photoluminescent phenomena and corresponding emission intensities at maximum wavelength of panthenol citrate oligomers (PAN-CA-IA-PEG) with different molar ratios (PAN;PEG) at 365 nm UV radiation. (c) Excitation intensities profile of panthenol citrates (PAN-CA) in $H_2O$ with different concentrations from 5 mg/ml to 100 mg/ml. (d) Photostability of panthenol citrate oligomers in $H_2O$ compared to quinine sulfate solution during shelf storage.
Figure 1:
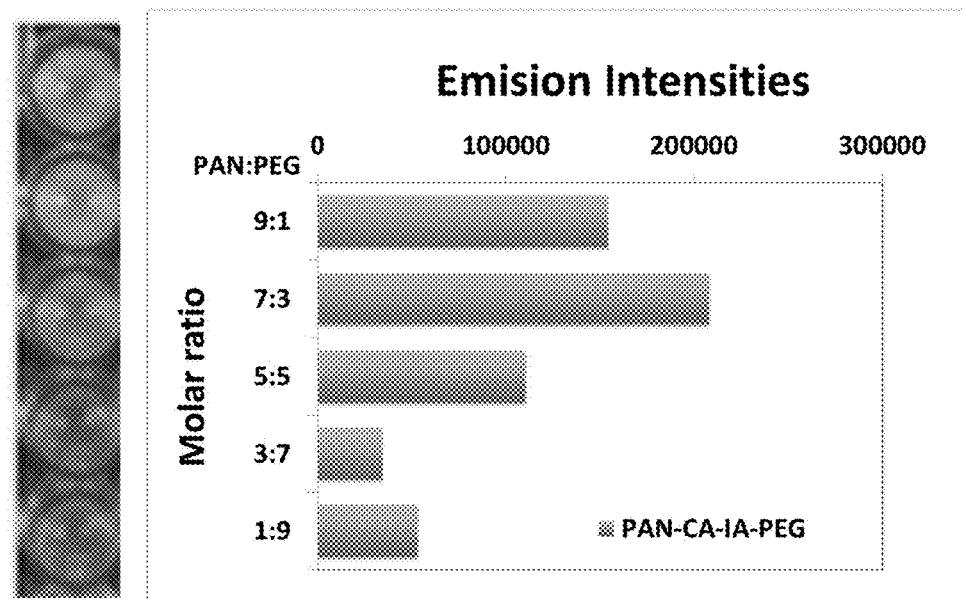
Figure 1:
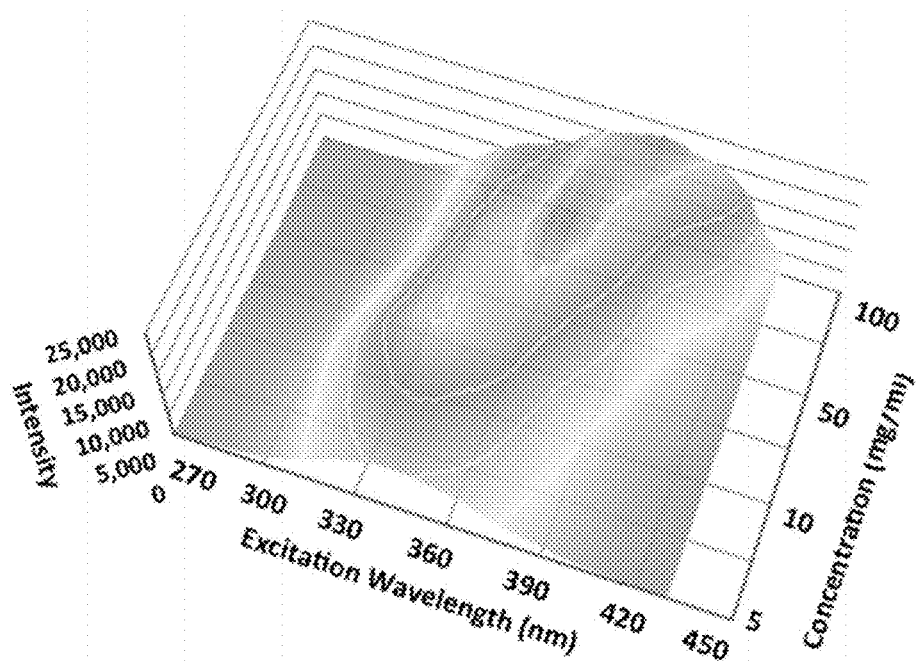
Figure 1:
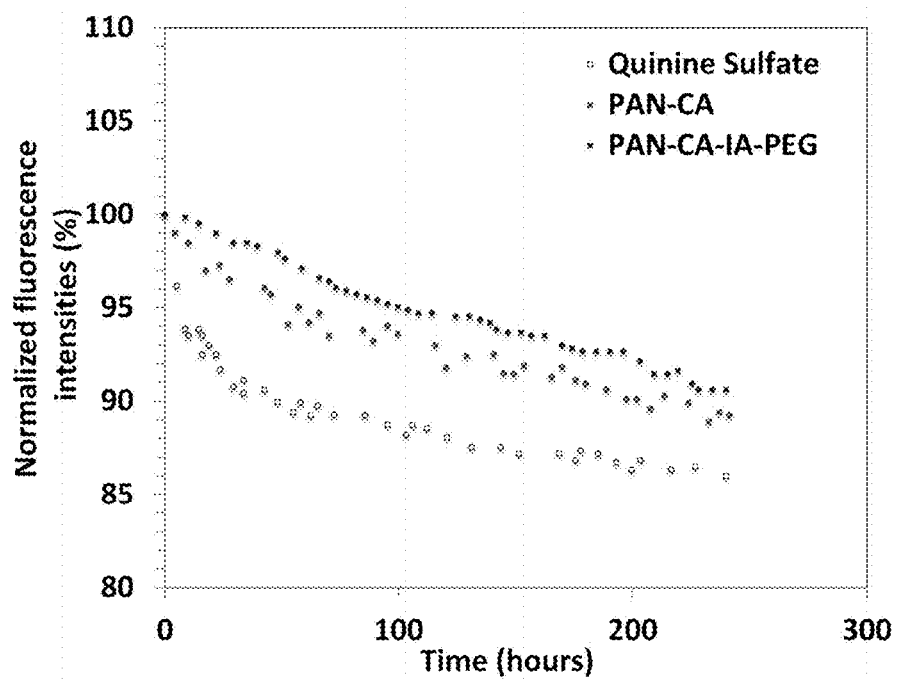

As used herein, the term "polymer" refers to a chain of repeating structural units or "monomers", typically of large molecular mass. Examples of polymers include homopolymers (single type of monomer subunits), copolymers (two types of monomer subunits), and heteropolymers (e.g., three or more types of monomer subunits). As used herein, the term "oligomer" refers to a polymer of only a few monomer units (e.g., 2, 3, 4, 5, or more) up to about 50 monomer units, for example a dimer, trimer, tetramer, pentamer, hexamer ... decamer, etc.

As used herein, the term "linear polymer" refers to a polymer in which the molecules form long chains without branches or crosslinked structures.

As used herein, the term "branched polymer" refers to a polymer comprising a polymer backbone with one or more additional monomers, or chains or monomers, extending from polymer backbone. The degree of interconnectedness of the "branches" is insufficient to render the polymer insoluble.

As used herein, the terms "pre-polymer" and "pre-oligomer" refer to linear or branched polymers and oligomers (e.g., not significantly crosslinked) that have the capacity to be crosslinked under appropriate conditions (e.g., to form a thermoset or hydrogel), but have not been subjected to the appropriate conditions.

As used herein, the term "crosslinked polymer" refers to a polymer with a significant degree of interconnectedness between multiple polymer strands, the result of which is an insoluble polymer network. For example, multiple polymer stands may be crosslinked to each other at points within their structures, not limited to the ends of the polymer chains.

As used herein, the term "hydrogel" refers to materials in which sufficient crosslinking is present to yield a polymer matrix that may be fully or partially swollen with water, one or more water-compatible alcohols, or combinations thereof. The crosslinking of the polymer matrix may be chemical or physical in nature. As non-limiting examples, the hydrogel may be crosslinked through covalent bonds, ionic interactions, hydrogen bonding, chain entanglement, or self-association of microphase segregating moieties. Additionally, one of skill in the art will readily understand that such hydrogels may exist and be used in a dehydrated (unswollen) state.

As used here, the terms "thermoset polymer" and "thermoset elastomer" refer to a polymer network that has exhibits a sufficient degree of covalent crosslinking to render the network insoluble (e.g., in both water and organic solvents) and infusible. "Thermosetting," the process of generating a "thermoset," may be achieved by thermal (e.g., heating), radiation (e.g., UV crosslinking), or chemical (e.g., chemically-induced crosslinking) means. The thermosetting procedure is not reversible, except by means of chemically breaking the covalent crosslinks.

As used herein, the term "substantially all," "substantially complete" and similar terms refer to greater than 99%; and the terms "substantially none," "substantially free of," and similar terms refer to less than 1%.

The term "about" allows for a degree of variability in a value or range. As used herein, the term "about: refers to values within 10% of the recited value or range (e.g., about 50 is the equivalent of 45-55).

The term "dermatologically acceptable," as used herein, means that the compositions or components thereof so described are suitable for use in contact with mammalian keratinous tissue without undue toxicity, incompatibility, instability, allergic response, and the like.

As used herein, "effective amount" means an amount of a composition sufficient to induce a intended or desired benefit. This means that the content and/or concentration of an active component of a formulation is sufficient that when the formulation is applied with normal frequency and in a normal amount, the formulation can result in the desired benefit.

The term "safe and effective amount" as used herein means an amount of a composition sufficient to induce an intended or desired benefit, but low enough to avoid undesired (e.g., serious) side effects (e.g., to provide a reasonable benefit to risk ratio, within the scope of sound judgment of the skilled artisan).

DETAILED DESCRIPTION

Provided herein are compositions comprising panthenol-citrate containing materials. In particular, panthenol citrate compounds, oligomers, and polymers, and methods of use and synthesis thereof, are provided herein.

Pantothenic acid (vitamin B5) and its reduced derivative, panthenol, have been studied and used for improving stratum corneum hydration, reducing trans-epidermal water loss (TEWL), and maintaining normal epithelial function. Topical application of panthenol at concentrations of 2-5% has been shown to stimulate the regeneration of injured skin (Wiederholt, et al. Experimental Dermatology, 2009. 18(11): p. 969-978; Ebner et al. Am J Clin Dermatol, 2002. 3(6): p. 7; herein incorporated by reference in their entireties). The toxicities of pantothenic acid and panthenol are negligible as no adverse reactions have been reported in any species even at large doses (Combs. Pantothenic Acid. 2012: p. 339-348; herein incorporated by reference in its entirety). Furthermore, pantothenate analogues or derivatives have been investigated to control the overall rate of CoA biosynthesis, demonstrating that derivative compounds of panthenol can have similar biological activity as the parent compound (Spry et al. PLoS One, 2013. 8(2): p. e54974; herein incorporated by reference in its entirety).

Citric acid is a reactive tricarboxylic acid that is part of the Krebs cycle and has been used as a key reactant monomer for the synthesis of polydiolcitrates with a wide range of properties and uses (Yang, J., et al., Synthesis and evaluation of poly(diol citrate) biodegradable elastomers. Biomaterials, 2006. 27(9): p. 1889-98; U.S. Pat. Nos. 8,772,437; 8,758,796; 8,580,912; 8,568,765; U.S. Pub. No. 2014/0155516; U.S. Pub. No. 2014/0135407; herein incorporated by reference in their entireties). Depending on the diol of choice, materials with controllable elasticity, biodegradability, and antioxidant properties can be developed (Serrano et al. Adv Mater, 2011. 23(19): p. 2211-5; Yang J., et al., A thermoresponsive biodegradable polymer with intrinsic antioxidant properties. Biomacromolecules, 2014. 15(11):3942-52; U.S. Pub. No. 2014/0037588; herein incorporated by reference in its entirety). Furthermore, the inclusion of amino acids in the reaction has been shown to confer photoluminescence properties to the resulting polymers that make them suitable for imaging and theranostic applications (Yang, J., et al., Development of aliphatic biodegradable photoluminescent polymers. Proc Natl Acad Sci USA, 2009. 106(25): p. 10086-91; herein incorporated by reference in its entirety).

Experiments were conducted during development of embodiments described herein to synthesize panthenol citrate oligoesters. The oligomers exhibit one or more (e.g., all) of the properties of: being optically active (e.g., light absorbing, light emitting, etc.), being antioxidants, being non-toxic, and maintaining the biologically desirable properties of panthenol. In some embodiments, pantheol citrate containing oligomers are photoluminescent chromophores. In addition to polymers and oligomers consisting of or consisting essentially of panthenol citrate, provided herein are panthenol citrate-based biomaterials (e.g., polymers and oligomers comprising pantheol citrate and other monomers (e.g., aliphatic diols, PEG, glycolic acid, lactic acid, malic acid, itaconic acid, glycerol 1,3-diglycerolate diacrylate, N-isopropylacrylamide, etc.), as well as methods of fabrication thereof. In some embodiments, panthenol-citrate-containing polymers and oligomers exhibit strong ultraviolet absorption, fluorescence and antioxidant properties. In some embodiments, panthenol citrate is incorporated into a wide array of polymers, including polyesters and polyurethanes. For example, biomaterials may be synthesized either via free radical polymerization with N-isopropylacrylamide to create thermoresponsive photoluminescent hydrogels, or condensation polymerization with a aliphatic diol to create photoluminescent elastomers. Biomaterials may be processed into photoluminescent nanoparticles, hydrogels, thermoplastics and elastomers that have applications in a variety of applications including skin protection, photothermal therapy, tissue engineering, wound healing, and fluorescence resonance energy transfer applications.

In some embodiments, provided herein are compounds, oligomers, polymers (e.g., polyesters, polyurethanes, etc.), elastomers (e.g., thermoset elastomers), etc. comprising as an element, a unit of the formula:

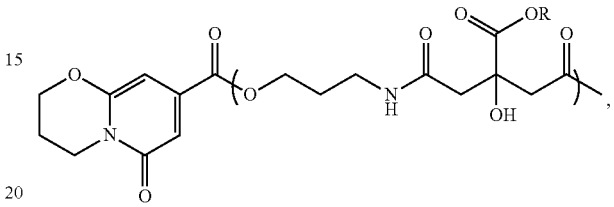

wherein R is H, pantoic acid, or β-alanol (a.k.a., 3-amino-1-propanol). The above unit may be referred to as panthenol citrate. The above unit may comprise two terminal H groups to form a panthenol citrate compound with a single chromophoric unit, or may comprise multiple (e.g., 2 to 1000, or more) repeating units. In some embodiments, a compound, oligomer, and/or polymer of panthenol citrate consists of or consists essentially of the above units (e.g., a homopolymer of panthenol citrate). In some embodiments, a polymer of panthenol citrate (e.g., consisting of panthnol citrate monomer units) is linear or branched.

In some embodiments, provided herein are panthenol citrate containing polymers, oligomers, hydrogels, thermosets, etc. Panthenol citrate (and/or the citric acid and panthenol components thereof) are reacted, oligomerized, and/or polymerized with one or more additional components (e.g., monomer units) to generate a hetero-oligomer or heteropolymer (e.g., comprising panthenol citrate and the one or more additional units). Any molecular entities capable of reacting with the reactive groups of panthenol and/or citritc acid may find use in the generation of oligomeric/polymeric compositions within the scope of the embodiments described herein. For example, panthenol citrate (and/or the citric acid and panthenol components thereof) are reacted, oligomerized, and/or polymerized with additional monomer groups (e.g., monomers), including, but not limited to: a lactide (e.g., D-lactide, L-lactide, or D,L-lactide), glycolide, lactone, carbonate, thiocarbonate, oxaketocycloalkane, thiooxaketocyclolakane, polyethylene glycol, glycerol, linear aliphatic diol (e.g., butanediol, hexanediol, octanediol, decanediol, dodecanediol, and shorter or longer linear aliphatic diols), linear aliphatic diacid (e.g., succinic acid, glutaric acid, adipic acid, pimelic acid, suberic acid, azelaic acid, sebacic acid, dodecanedioic acid, and shorter or longer linear aliphatic diacids), citric acid, isocitric acid, aconitic acid, propane-1,2,3-tricarboxylic acid, trimesic acid, diols, triols, polyols, itaconic acid, maleic acid, maleic anhydride, glycerol 1,3-diglycerolate diacrylate, glycerol dimethacrylate, 3-(acryloyloxy)-2-hydroxypropyl methacrylate, N-isopropylacrylamide, etc.

In some embodiments, oligomers and polymers comprising panthenol citrate comprise at least 0.1% monomers of panthenol citrate (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, oligomers and polymers comprising panthenol citrate comprise less than % monomers of panthenol citrate (e.g., <99%, <98%, <95%, <90%, <80%, <70%, <60%, <50%, <40%, <30%, <20%, <10%, <5%, <4%, <3%, <2%, <1%, <0.5%,). In some embodiments, oligomers and polymers comprising panthenol citrate comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% panthenol citrate monomers.

In some embodiments, provided herein are composites of the panthenol citrate compounds, oligomers, polymers, hydrogels, and thermosets described herein with additional components. For example, panthenol citrate materials may be used with one or more biodegradeable polymers to form a panthenol citrate composite material. Suitable biodegradeable polymers include, but are not limited to: collagen, elastin, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), poly (diol citrate) (e.g., poly(octanediol citrate), etc.), casein, dextran and derivatives, polysaccharides, poly(caprolactone), fibrinogen, poly(hydroxyl acids), poly(L-lactide) poly (D,L lactide), poly(D,L-lactide-co-glycolide), poly(L-lactide-co-glycolide), copolymers of lactic acid and glycolic acid, copolymers of ε-caprolactone and lactide, copolymers of glycolide and ε-caprolactone, copolymers of lactide and 1,4-dioxane-2-one, polymers and copolymers that include one or more of the residue units of the monomers D-lactide, L-lactide, D,L-lactide, glycolide, ε-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly(hydroxyvaleric acid), polydioxanone, poly(ethylene terephthalate), poly (malic acid), poly(tartronic acid), polyanhydrides, polyphosphazenes, poly(amino acids), and copolymers of the above polymers as well as blends and combinations of the above polymers. (See generally, Illum, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986; herein incorporated by reference in their entireties). Composites may also be made of panthenol citrate and a non-biogregradable polymer, such as: silicone rubber, polyethylene, acrylic resins, polyurethane, polypropylene, and polymethylmethacrylate. Composites of panthenol citrate and non-polymeric materials are also within the scope of embodiments described herein. Such non-polymer components include, but are not limited to a bioceramic (e.g., hydroxyapatite, tricalcium phosphate, etc.), nanoparticles (e.g., iron oxide, zinc oxide, gold, etc.), cosmetic ingredients (e.g., glycerin, glyceryl dilaurate, diisobutyl adipate, mineral oil, dimethicone, pentylene glycol, cyclopentasiloxane, etc.) and tattoo inks (e.g. glycerin, propylene glycol, etc.)

In some embodiments, a panthenol citrate composite material comprises at least 0.1% panthenol citrate (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, a panthenol citrate composite material comprises less than 99% panthenol citrate (e.g., <99%, <98%, <95%, <90%, <80%, <70%, <60%, <50%, <40%, <30%, <20%, <10%, <5%, <4%, <3%, <2%, <1%, <0.5%,). In some embodiments, a panthenol citrate composite material comprises panthenol citrate in an amount of about 99%, about 98%, about 95%, about 90%, about 80%, about 70%, about 60%, about 50%, about 40%, about 30%, about 20%, about 10%, about 5%, about 4%, about 3%, about 2%, about 1%, about 0.5%, or ranges therein. The aforementioned percentages may be wt % or molar %.

In some embodiments, synthesis of the compounds, oligomer, polymers, etc. described herein are produced by combination of the component molecules (e.g., citric acid, panthenol, etc.) under the appropriate conditions (e.g., temperature, pressure, pH, etc.). In some embodiments, reaction, oligomerization, polymerization, etc. occurs upon combination of the components under appropriate conditions in the absence of any additional enzyme or chemical catalysts.

In some embodiments, components (e.g., citric acid, panthenol, etc.) are heated to at least 60° C. (e.g., >60° C., 70° C., 80° C., 90° C., 100° C., 110° C., 120° C., 130° C., 140° C., 150° C., 160° C., 170° C., 180° C., or more). In some embodiments, components (e.g., citric acid, panthenol, etc.) are reacted at a temperature not exceeding 250° C. (e.g., <240° C., 220° C., 200° C., 180° C., 160° C., or less). In some embodiments, components (e.g., citric acid, panthenol, etc.) are reacted at a temperature between 60° C. and 180° C. (e.g., 60° C., 70° C., 80° C., 90° C., 100° C., 110° C., 120° C., 130° C., 140° C., 150° C., 160° C., 170° C., 180° C., and ranges therein). In some embodiments, components (e.g., citric acid, panthenol, etc.) are reacted at a temperature of about 120° C.

In some embodiments, components (e.g., citric acid, panthenol, etc.) are reacted at a pressure of less than 200 mBar (e.g., <200 mBar, <150 mBar, <100 mBar, <50 mBar, <20 mBar, <10 mBar, or less) or at an inert atmosphere (e.g., $N_2$, Ar, etc.).

In some embodiments, components (e.g., citric acid, panthenol, etc.) are reacted for at least 1 minute (e.g., >1 minute, >2 minutes, >3 minutes, >4 minutes, >5 minutes, >10 minutes, >20 minutes, >30 minutes, >45 minutes, >1 hour, >2 hours, >3 hours, >4 hours, >12 hours, or more).

In some embodiments, citric acid and panthenol are reacted at equimolar concentrations. In some embodiments, citric acid and panthenol are reacted at a ratio of 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10. In some embodiments, in a single reaction vessel, additional reactant(s) (e.g., one or more of PEG, an aliphatic diol, itaconic acid, etc.) are included at a ratio of 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 to either the citric acid or pantenol in the reaction.

In some embodiments, methods of generating panthenol citrate materials comprise a multiple step (e.g., two step) reaction procedure. In some embodiments, a first step comprises reacting, oligomerizing, or polymerizing citric acid and panthenol (e.g., at about equimolar concentration, 80-160° C., <200 mBar, >1 hour, etc.) to generate a panthenol citrate compound, oligomer, or polymer (e.g., PAN-CA). In some embodiments, a first step comprises reacting, oligomerizing, or polymerizing citric acid, panthenol, and one or more additional agents described herein to generate a panthenol citrate compound, oligomer, or polymer (e.g., PAN-CA-IA, PAN-CA-PEG, PAN-CA-AD (e.g., PAN-CA-OD), etc). In some embodiments, a second step comprises reacting PAN-CA generated in the first step with an additional compound. In some embodiments, a second step comprises reacting a panthenol citrate compound, oligomer, or polymer (e.g., PAN-CA-IA, PAN-CA-PEG, PAN-CA-AD (e.g., PAN-CA-OD), etc.) with an additional compound (e.g., N-isopropylacrylamide). In some embodiments, a second (or subsequent) step comprises incubating a material (e.g., PAN-CA-AD (e.g., PAN-CA-OD)) at a lower temperature (e.g., 40-120° C.) for crosslinking of oligomer or polymer strands (e.g., to form a thermoset elastomer).

Various functional groups may be introduced into and/or appended onto the compound, oligomers, and/or polymers described in embodiments herein, for example to impart desirable structural, physical, chemical, physiochemical and/or biological properties to the material. Suitable functional groups may include targeting moieties (e.g., peptide, aptamer, antibody, epitope, etc.), detectable moieties (e.g., fluorescent dye, contrast agent, radionuclide, metal ion, etc.), interaction moiety (e.g., biotin, streptavidin, crosslinkable moiety, etc.), localization signal (e.g., cellular or nuclear localization signal), etc.

In some embodiments, provided herein are methods of incorporating the panthenol-citrate-containing compounds, oligomers, and polymers described herein into composites, other materials, and formulations for specific applications. Compositions described herein find use in a variety of fields and application, including, but not limited to: photoactive dyes or molecular probes based on panthenol citrate, therapeutic agents in antibiotics and metabolism-associated diseases, water-soluble UV absorber and an active ingredient for UV protection, in-situ injectable embolism of arteriovenous malformation and aneurysm, in-situ encapsulation and injectable carrier of drug, protein, transgene and cells; photoluminescent epidermal devices, etc.

In some embodiments, the panthenol-citrate-containing compounds, oligomers, and polymers described herein are formulated for application to human or animal skin (e.g., for protection from sun exposure). In such embodiments, compositions and formulations may comprise one or more additional active or inactive ingredients. For instance, such materials may be selected from the group consisting of sugar amines (e.g., N-acetylglucosamine), vitamin B3 compounds, sodium dehydroacetate, dehydroacetic acid and its salts, phytosterols, soy derivatives (e.g., equol and other isoflavones), niacinamide, phytantriol, farnesol, bisabolol, salicylic acid compounds, hexamidines, dialkanoyl hydroxyproline compounds, flavonoids, N-acyl amino acid compounds, retinoids (e.g., retinyl propionate), water-soluble vitamins, ascorbates (e.g., vitamin C, ascorbic acid, ascorbyl glucoside, ascorbyl palmitate, magnesium ascorbyl phosphate, sodium ascorbyl phosphate), particulate materials, sunscreen actives, anti-cellulite agents, butylated hydroxytoluene, butylated hydroxyanisole, their derivatives, and combinations thereof. Other examples of optional ingredients can include cationic polymers, conditioning agents (hydrocarbon oils, fatty esters, silicones), anti-dandruff agents, antiseborrheic agents, antipsoriasis agents, suspending agents, viscosity modifiers, dyes, nonvolatile solvents or diluents (water soluble and insoluble), pearlescent aids, foam boosters, surfactants, nonionic cosurfactants, pediculocides, pH adjusting agents, perfumes, preservatives, chelants, chelating agents, proteins, UV absorbers, pigments, other amino acids, and other vitamins.

Compositions and formulations may comprise one or more vitamins and/or amino acids such as: water soluble vitamins such as vitamin B1, B2, B6, B12, C, pantothenic acid, pantothenyl ethyl ether, biotin, and their derivatives, water soluble amino acids such as asparagine, alanine, indole, glutamic acid and their salts, water insoluble vitamins such as vitamin A, D, E, and their derivatives, water insoluble amino acids such as tyrosine, tryptamine, and their salts.

Compositions and formulations may also contain one or more pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names. The compositions may also contain antimicrobial agents which are useful as cosmetic biocides and antidandruff agents including: water soluble components such as piroctone olamine, water insoluble components such as 3,4,4'-trichlorocarbanilide (trichlosan), triclocarban and zinc pyrithione.

Any other suitable optional component can also be included in compositions within the scope of embodiments described herein, such as those ingredients that are conventionally used in given skin care products types. The CTFA Cosmetic Ingredient Handbook, Tenth Edition (published by the Cosmetic, Toiletry, and Fragrance Association, Inc., Washington, D.C.) (2004) (hereinafter "CTFA"; herein incorporated by reference in its entirety), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antibacterial agents, antifungal agents, antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, plant derivatives, plant extracts, plant tissue extracts, plant seed extracts, plant oils, botanicals, botanical extracts, preservatives, propellants, reducing agents, sebum control agents, sequestrants, skin bleaching and lightening agents, (e.g. hydroquinone, kojic acid, ascorbic acid, magnesium ascorbyl phosphate, ascorbyl glucoside, pyridoxine), enzymes, coenzymes, skin-conditioning agents (e.g. humectants and occlusive agents), skin soothing and/or healing agents and derivatives (e.g. panthenol, and derivatives such as ethyl panthenol, aloe vera, pantothenic acid and its derivatives, allantoin, bisabolol, and dipotassium glycyrrhizinate), skin treating agents (e.g. vitamin D compounds, mono-, di-, and tri-terpenoids, beta-ionol, cedrol), thickeners, and vitamins and derivatives thereof.

More detailed description of components of skin care compositions (e.g., for use in sunscreens) may be found in, for example, U.S. Pat. No. 8,871,717; herein incorporated by reference in its entirety).

Materials described herein (e.g., panthenol-citrate containing compounds, oligomers, and polymers) also find use as implants (e.g., medical implants), substrates (e.g., for cell growth), etc. In some embodiments, objects are constructed out of the materials described herein, and/or out of materials including those described herein. In some embodiments, the properties of the materials described herein (e.g., photoactivity, biocompatibility, structural characteristics, etc.) are imparted to the implants for use within a human or animal subject.

Materials described herein also find use as coatings (e.g., biocompatible coating) for devices (e.g., medical devices, implantable devices, etc.). The properties of the materials described herein (e.g., photoactivity, biocompatibility, structural characteristics, etc.) are imparted to the devices (e.g., for use with a human or animal subject).

Materials described herein also find use in diagnostic, clinical, therapeutic, molecular biology, biochemical, and/or biophysical applications, for example as a detectable agent (e.g., dye, marker, etc.), structural material, delivery agent, etc.

In some embodiments, contact lenses comprising one or more materials described herein (e.g., panthenol-citrate containing compounds, oligomers, and polymers) are provided. In some embodiments, materials described herein (e.g., panthenol-citrate containing compounds, oligomers, and polymers) are the base material for a contact lens. In other embodiments, contact lenses are made of a composite of materials described herein (e.g., panthenol-citrate containing compounds, oligomers, and polymers) and other materials (e.g., traditional contact lens materials, such as: polymacon, silicone hydrogels, etc.). In some embodiments, materials described herein (e.g., panthenol-citrate containing compounds, oligomers, and polymers) are coated onto a contact lens. In some embodiments, the presence of materials described herein (e.g., panthenol-citrate containing compounds, oligomers, and polymers) in a contact lens confers antioxidant and UV absorption(resistance) properties to the lenses.

In some embodiments, protective packaging materials (e.g., for packaging of UV- or oxidation-sensitive goods (e.g., food)) comprising one or more materials described herein (e.g., panthenol-citrate containing compounds, oligomers, and polymers) are provided. In some embodiments, materials described herein (e.g., panthenol-citrate containing compounds, oligomers, and polymers) are the base material for the packaging. In other embodiments, packaging materials comprise a composite of materials described herein (e.g., panthenol-citrate containing compounds, oligomers, and polymers) and other packaging materials. In some embodiments, materials described herein (e.g., panthenol-citrate containing compounds, oligomers, and polymers) are coated onto packaging materials. In some embodiments, the presence of materials described herein (e.g., panthenol-citrate containing compounds, oligomers, and polymers) in/on packaging materials confers antioxidant and UV absorption (resistance) properties to the lenses.

In some embodiments, materials described herein (e.g., panthenol-citrate containing compounds, oligomers, and polymers) find use in the monitoring of the presence or exposure to free radicals through fluorescence measurements. In some embodiments, as materials described herein (e.g., panthenol-citrate containing compounds, oligomers, and polymers) are exposed to free radicals, the antioxidant capacity of the materials are reduced. Since fluorescence and antioxidant capacity of the materials have been shown to be proportional, residual fluorescence of a material following a use is inversely proportional to the free-radical exposure experienced by the material.

EXPERIMENTAL

Example 1

Materials

Citric acid (CA, 99%), Itaconic acid (IA, ≥99%), DL-panthenol (PAN, 99%), Polyethylene glycol (PEG, 200), 1,8-Octanediol (OD, 98%), Glycerol 1,3-diglycerolate diacrylate (GDD, technical grade), 2,2'-Azobisisobutyronitrile (AIBN, 98%), Tetrahydrofuran (THF, 99%) were purchased from Sigma-Aldrich. N-isopropylacrylamide (NIPAAm, 98%) was purchased from TCI America and purified by recrystallization in hexane and dried under vacuum.

Synthesis of Panthenol Citrate Oligoesters

Equimolar amounts of panthenol and citric acid (1:1) were added to a round-bottom flask and heated up to 120° C. under vacuum (<100 mBar) or $N_2$. After melting, the mixture was reacted at this temperature for 2 hours. The obtained oligomer was purified via dissolution and precipitation in ethanol and acetone followed by drying under vacuum. To synthesize oligomers for the synthesis of thermoresponsive hydrogels (Yang J., et al., A thermoresponsive biodegradable polymer with intrinsic antioxidant properties. Biomacromolecules, 2014. 15(11):3942-52; U.S. Pub. No. 2014/0037588; herein incorporated by reference in its entirety), polyethylene glycol and itaconic acid (or glycerol 1,3-diglycerolate diacrylate) were added to the reaction mixture at the molar feed ratio described below. To synthesize oligomers for the synthesis of elastomers, 1,8-octanediol was added to the reaction mixture at the molar feed ratio described below. Although we obtained oligomers by reacting PAN with several alpha-hydroxyacids (glycolic acid, lactic acid, malic acid, itaconic acid), none of these were fluorescent.

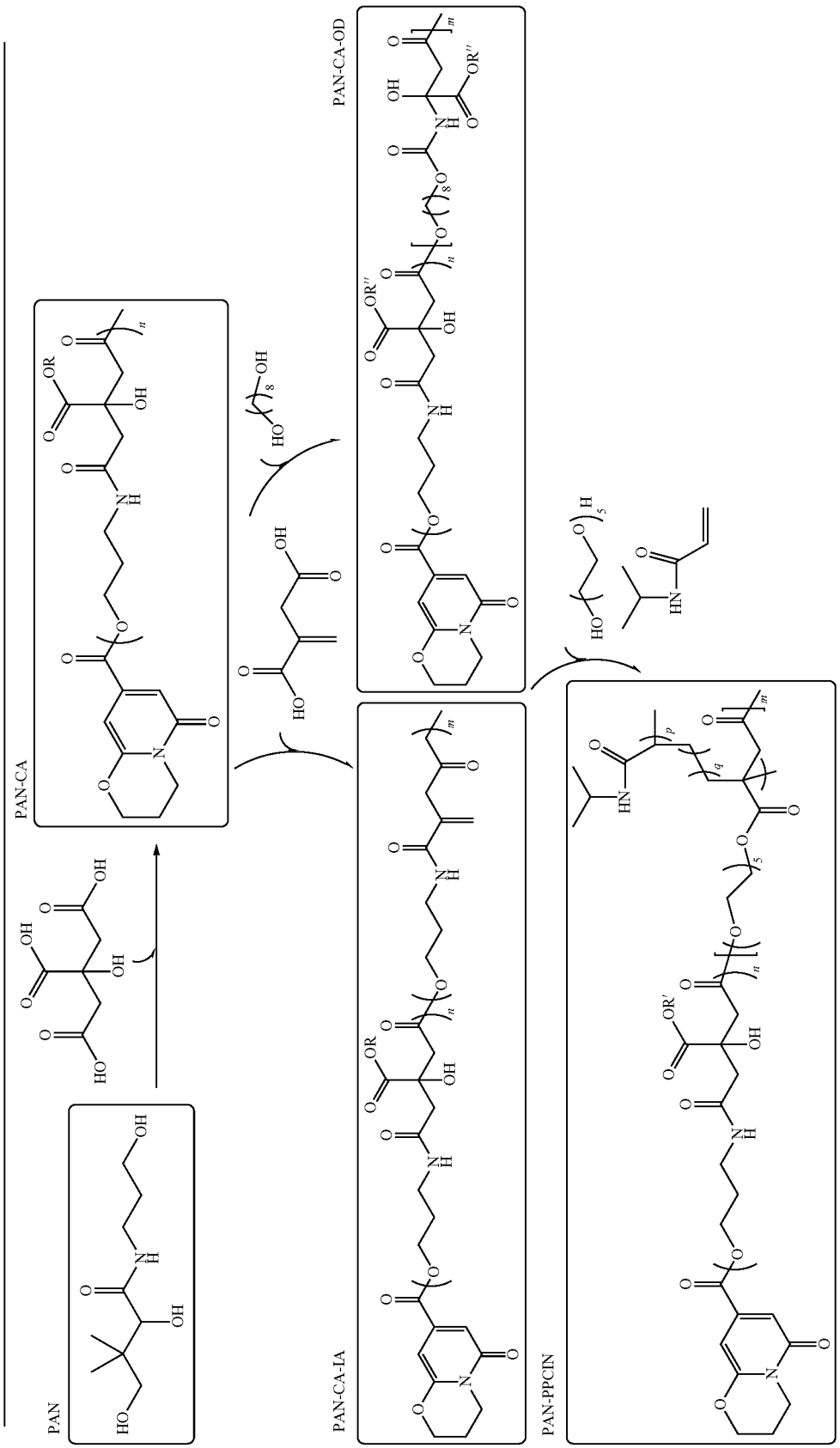
Scheme 1. Exemplary condensation polymerization of panthenol and citric acid, and condensation copolymerization with Itaconic acid and 1,8-octanediol, as well as free radication polymerization with polyethylene glycol and N-isopropylacrylamide.

Photoluminescent and Ultraviolet Absorption Properties

The photoluminescent properties of the oligomers were investigated on a PC1 photon counting spectrofluorometer (ISS, Champaign, Ill.). The slit widths of both excitation and emission were set at 0.5 nm for all samples except where otherwise indicated. Fluorescent intensity of the oligomers in pure form or in aqueous solution (10 mg/ml) was recorded at 440 nm for emission excited at 350 nm and 365 nm, respectively. Rhodamine B solution in ethanol and quinine sulfate in perchloric acid were used as references to assess photostability of oligomers over time. Ultraviolet absorption spectra were recorded using a Agilent Cary 100 UV/Vis spectrophotometer (Agilent, Senta Clara, Calif.) from 200 nm to 700 nm.

Figure 13:
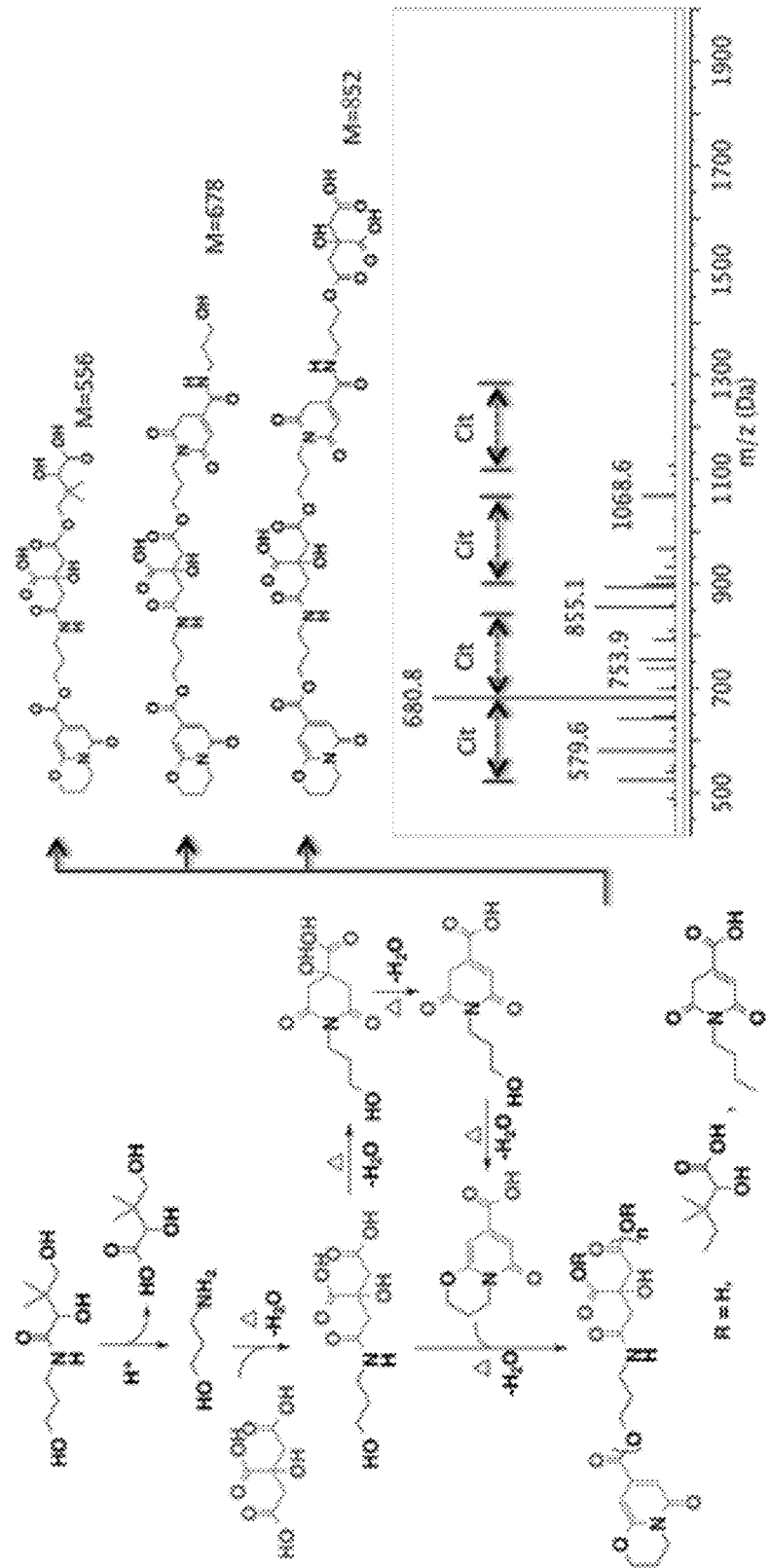
FIG. 13. The reaction mechanism of panthenol citrate was confirmed by electrospray ionization mass spectrometry.

Chemical Characterization of Panthenol Citrate $^1$H, $^{13}$C and COSY spectra of panthenol citrate were recorded using a Ag500 NMR spectrometer (Bruker, Billerica, Mass.) at ambient temperature, using DMSO as solvent and tetramethylsilane (TMS) as an internal reference. FID resolution was 0.158 Hz/point, corresponding to a sweep width of 10.3 kHz and acquisition time of 3.07 sec. The molecular weight and distribution of panthenol citrate were measured by Autoflex III Smartbeam Matrix-assisted laser desorption ionization (MALDI) mass spectrometry (Bruker, Billerica, Mass.) and analyzed in positive mode using α-Cyano-4-hydroxycinnamic acid (α-CHCA) as a matrix, to further investigate the reaction mechanism of panthenol citrate, the reacted oligomer was eluted in a butanol/ethanol/ammonia hydroxide/water mixture and detected by Aligent HPLC-ESI-MS system equipped with C18 Column and PDA detector, TQD mass spectrometer was used to detect all the fractions in a scan mode ranging from 50 to 1000 m/z (FIG. 13). Attenuated total reflection-Fourier transform infrared (ATR-FTIR) spectra were obtained in Thermo Nicolet Nexus 870 spectrometer equipped with a Pike horizontal ATR accessory with a covered sample trough, using 8 cm$^{-1}$ spectral resolution and accumulation of 64 scans, the reflectance element was a ZnSe crystal with ten internal reflections. The ATR element was covered with 500 ul of each oligomer solution with a concentration of 10 mg/ml.

Effect of Panthenol Citrate Oligomers on Cell Viability in Vitro

Human umbilical vein endothelial cells (HUVEC) (Lonza, Walkersville, Md.), adult human epidermal keratinocytes (HEKa) (Gibco, Carlsbad, Calif.), and human dermal fibroblast (HDF) (Lonza, Walkersville, Md.) were cultured in SmGM-2, Keratinocyte-SFM and DMEM, respectively, in a humidified incubator equilibrated with 5% $CO_2$ at 37° C. Cells were seeded at a density of $1\times10^4$ cells/ml in 96-well tissue culture plates. Panthenol citrate oligomers were dissolved in sterile PBS (10 mg/ml) and diluted from 0.01 to 5 mg/ml with culture media and added to the cells to evaluate cytotoxicity.

Synthesis of Thermoresponsive Hydrogels Based on Panthenol Citrate Oligomers

Panthenol polyethylene glycol citrate-co-itaconate (PAN-PEG-CA-IA) oligomers with a molar ratio 0.1:0.9:0.8:0.2 were synthesized as described above. Water-soluble thermoresponsive photoluminescent hydrogels were synthesized by free radical polymerization by reacting PAN-CA-IA-PEG with NIPAAm. Briefly, equivalent amounts of PAN-PEG-CA-IA and NIPAAm ($6.5\times10^{-3}$ M in concentration) were added into a three-neck round-bottom flask and reacted in THF at 65° C. for 8 hours in a nitrogen atmosphere, using AIBN as an initiator. The obtained poly(panthenol polyethylene glycol citrate itaconate-co-N-isopropylacryamide) (PAN-PPCIN) copolymer was dissolved in 1,4-dioxane and purified by precipitation in diethyl ether and vacuum dried. Poly(polyethylene glycol citrate itaconate-co-N-isopropylacrylamide) (PPCIN) without panthenol was synthesized via the same method as a reference material.

Particle Size, Phase Transition and Viscoelastic Behavior of Panthenol Citrate Hydrogels Particle characterization was performed via nanoparticle tracking analysis on a NanoSight NS300 (Malvern, Worcestershire, UK) at 25° C. The pH of panthenol citrate oligomers was adjusted to 7.4 using NaOH or HCl and the material was reconstituted in nanopure water at a series of dilutions and filtered through a 5 μm syringe filter. Lower critical solution temperature (LCST) of PAN-PPCIN hydrogel with 10 mol % panthenol was measured in a Jasco-815 circular dichroism (CD) spectrophotometer (Jasco, Easton, Md.) by monitoring the transmittance. The absorbance at 450 nm was measured at 1° C./min from 15 to 45° C. and the temperature at 50% transmittance was defined as the LCST. The viscoelastic properties of neutralized PPCIN and PAN-PPCIN hydrogels with 100 mg/ml in PBS were studied in a Discovery® Hybrid DHR-3 (TA, New castle, Del.) rheometer. The analyses were conducted at a frequency of 1.5 Hz and a heating rate of 2° C./min, using a 1.5% strain and a 50 rad/s angular frequency, in the temperature range from 15° C. up to 45° C. Storage modulus (G') and loss modulus (G") changes of PPCIN and PAN-PPCIN solutions were recorded.

Effect of Panthenol Citrate Thermoresponsive Hydrogel on Cell Viability

To measure the cytotoxity, PPCIN and PAN-PPCIN were sterilized with ethylene oxide and neutralized to pH 7.4 before reconstitution in sterilized PBS (100 mg/mL). HUVEC, HEKa and HDF cells ($1.0\times10^4$ cells/mL) were added to 48-well ultra-low attachment plates (Corning, N.Y.) and the cooled polymer solutions were added to the cells. After gelation for 30 min at 37° C., warm media was added. Viability was assessed after 24 hours of culture using the Live/Dead assay according to manufacturer's instructions.

Synthesis and Mechanical Characterization of Panthenol Citrate Elastomers

The prepolymer panthenol octanediol citrate (PAN-OD-CA), referred to as PPOC, with a molar composition of 0.1:0.9:1 was synthesized as described above. Elastomeric poly(panthenol octanediol citrate) films were prepared via post-polymerization of PAN-OD-CA at 60° C. for 5 days. Poly(1,8 octanediol citrate) (POC) (Yang et al. Biomaterials, 2006. 27(9): p. 1889-98; herein incorporated by reference in its entirety) with a molar composition of 1:1 was also synthesized and used as a reference material. Tensile tests were performed according to ASTM D1621 standard. POC and PPOC elastomers with 10 mol % and 20 mol % panthenol were processed into strips (26 mm×4 mm×0.5 mm, length×width×thickness), and the cross head speed was set at 50 mm/min. All tests included at least 3 samples. POC and PPOC elastomers were coated on the 12-well plates and incubated with 1 ml $H_2O$ to monitor in vitro panthenol release. Supernatants were collected and detected via a Shimadzu LCMS-2020 high performance liquid chromatography (HPLC) (Shimadzu, Kyoto, Japan) equipped with Ascentis C18 column (15 cm×2.1 mm, 3 um particle size, Sigma Aldrich, St. Louis, Mo.) at a flow rate of 1 ml/min using methanol and phosphate buffer solution (pH=2.5) as a mobile phase.

UVA Radiation Protective Properties of Panthenol Citrate Hydrogels

Endothermic phase changes of PPCIN and PAN-PPCIN hydrogel (100 mg/ml pH=7.4) were investigated under direct exposure to UVA radiation (365 nm) (ELC-251 Ultraviolet Source, Electro-Lite Corporation). Irradiance was measured via digital solar power meter to be 230 mW/cm$^2$. The excised skin from 6-month-old female pigs, killed at a slaughterhouse, was cut under sterile conditions into 6×6 cm$^2$ pieces. To avoid dehydration, the explants were placed in a petri dish and embedded in 4-(2-hydroethyl)-1-piperazine ethanesulfonic acid (HEPES)-agar (145 mM NaCl, 5 mM KCl, 1 mM MgSO$_4$, 10 mM HEPES, 10 mM glucose, 5% agarose, pH=7.5). The surface of the pig's skin was covered by aluminum foil that had 10 mm diameter holes. 500 ul of PPCIN and PAN-PPCIN hydrogel were placed on some of the holes and the skin was exposed to 365 nm irradiation for 15 minutes. The exposed skin was embedded in OCT for cryosectioning, snap-frozen, and investigated via routine Hemotoxylin-Eosin (H&E) staining after sectioning.

Antioxidant Properties and Fluorescence Quenching

Adult human epidermal keratinocytes (HEKa) were seeded in Greiner® UV-star transparent plates and exposed to a 6W UVL-56 handheld UV lamp (UVP Inc, Calif.) at 365 nm. UV light activates reactive oxygen species (ROS). The irradiance in the plate was measured with a hand-held model 1918-C optical meter (Newport, Irvine, Calif.). Before UV exposure, keratinocyte cells were treated with 1 mg/ml panthenol citrate. Dihydroethidium (DHE) was incubated with treated keratinocytes for 1 hour and fluorescence was recorded at a 2 sec exposure time using a Eclipse TE2000 Epi-fluorescence microscope (Nikon, Tokyo, Japan). The hydrophilic radical cation (2,2'-azino-bis(3-ethylbenzthiazoline-6-sulphonic acid) (ABTS) was used to test the free radical scavenging capacity of panthenol citrate and the hydrogels. The oligomers (50 mg/mL) were exposed to ABTS solution and incubated at 37° C. At each time point, the ABTS solution was sampled, diluted with MQ water 1:1 and the absorbance measured at 734 nm. Measurements were performed in triplicate. The antiradical activity was measured as % inhibition of free radicals by measuring the decrease in absorbance compared to control solutions. The antiradical activity was measured as % inhibition of free radicals by measuring the decrease in absorbance compared to control solutions. Fluorescence quenching experiments were performed in UVP® transilluminator dark room, 0.001M to 0.2M TEMPO radical, Fe$^{2+}$/H$_2$O$_2$, Ascorbic acid and EDTA were used to evaluate the changes of fluorescence intensities of 0.1 mg/ml panthenol citrate.

Example 2

Experiments conducted during development of embodiments described herein demonstrate the synthesis of cytocompatible oligochromophore from panthenol and citric acid, as well as biomaterials that are based on the oligochromophore. The oligochromophore is unique in that it is only produced when panthenol is reacted with citric acid and not with other α-hydroxy acids such as glycolic acid, DL-lactic acid, DL-malic acid, as well as itaconic acid and tricarballylic acid, and has very strong absorption in the UVA and UVB radiation ranges. The oligochromophores are relatively viscous and water-soluble, with an aciditiy of 3.2±0.2. Compared to quinine sulfate, the oligochromophores show excellent photostability under continuous illumination at 350 nm for 10 minutes, even after storage at room temperature for 10 days (e.g., no significant photobleaching was observed).

Figure 2:
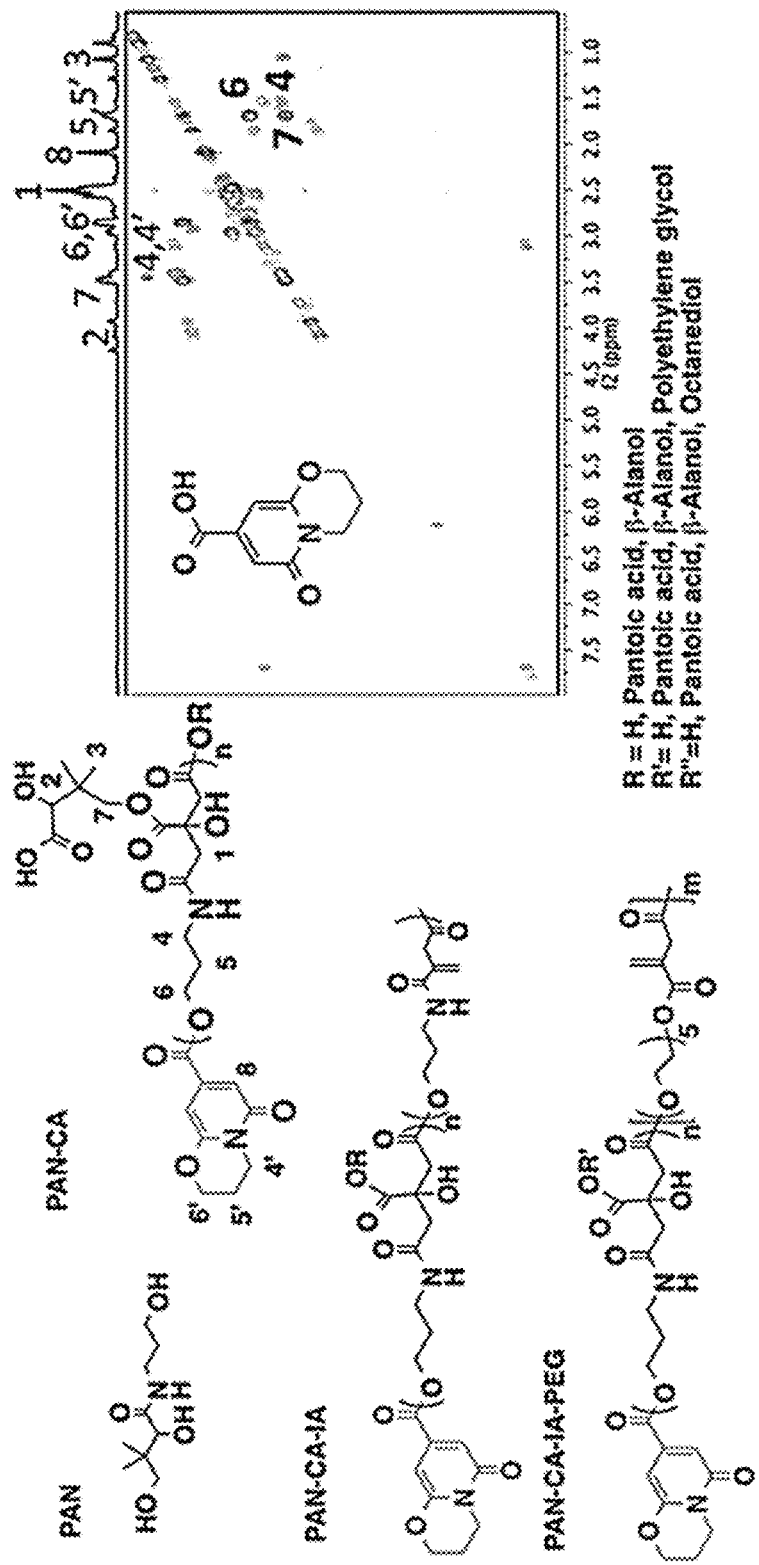
FIG. 2. Chemical structures and ATR-FTIR spectra of PAN-CA, PAN-CA-IA (1:0.8:0.2) and PAN-CA-IA-PEG (0.5:0.8:0.2:0.5) oligomers, and structure identification of the chromophore in two dimensional proton nuclear magnetic resonance correlation spectra (2D NMR COSY) of panthenol citrate (OPC) in DMSO-d.
Figure 2:
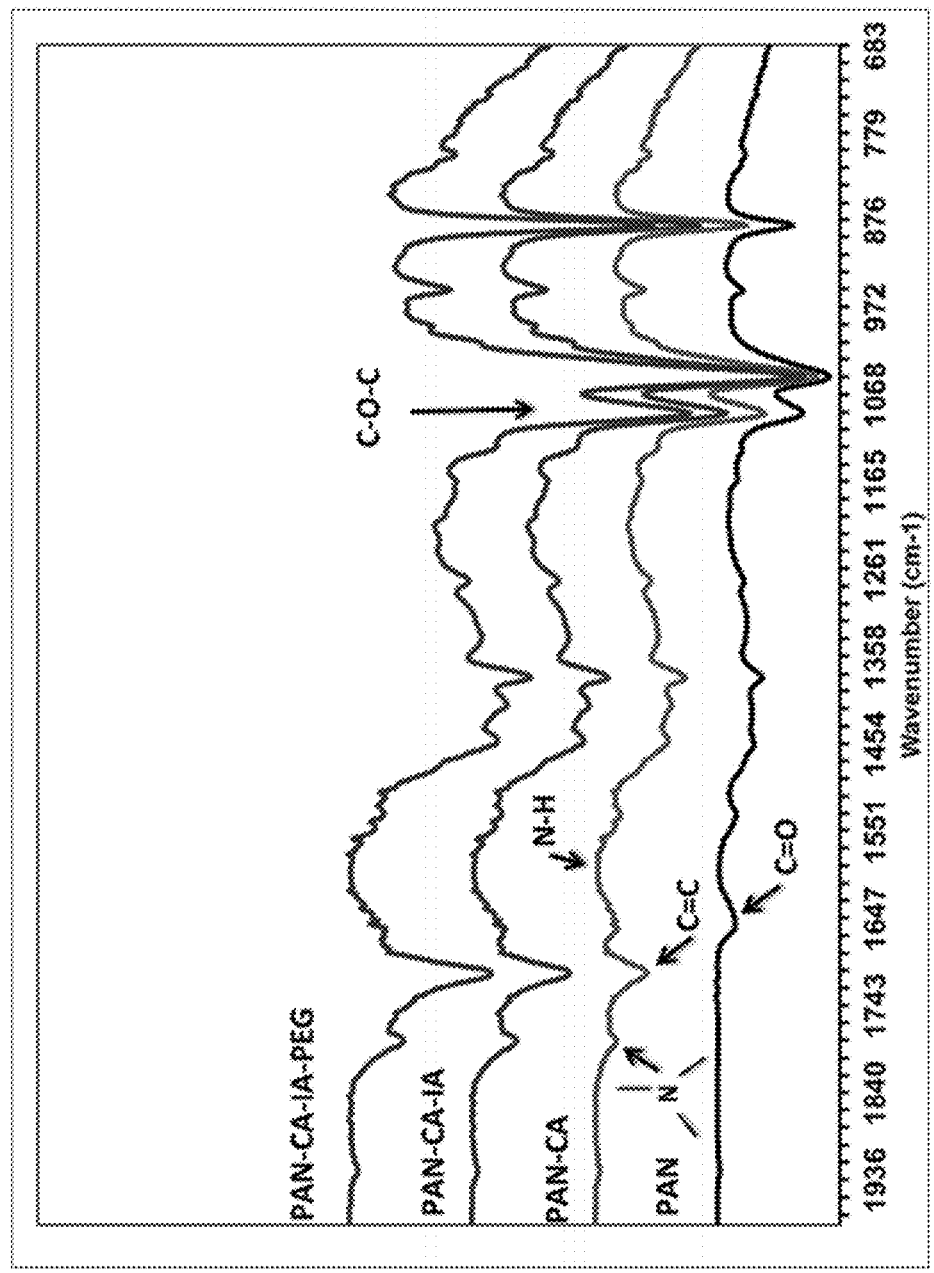
Figure 14:
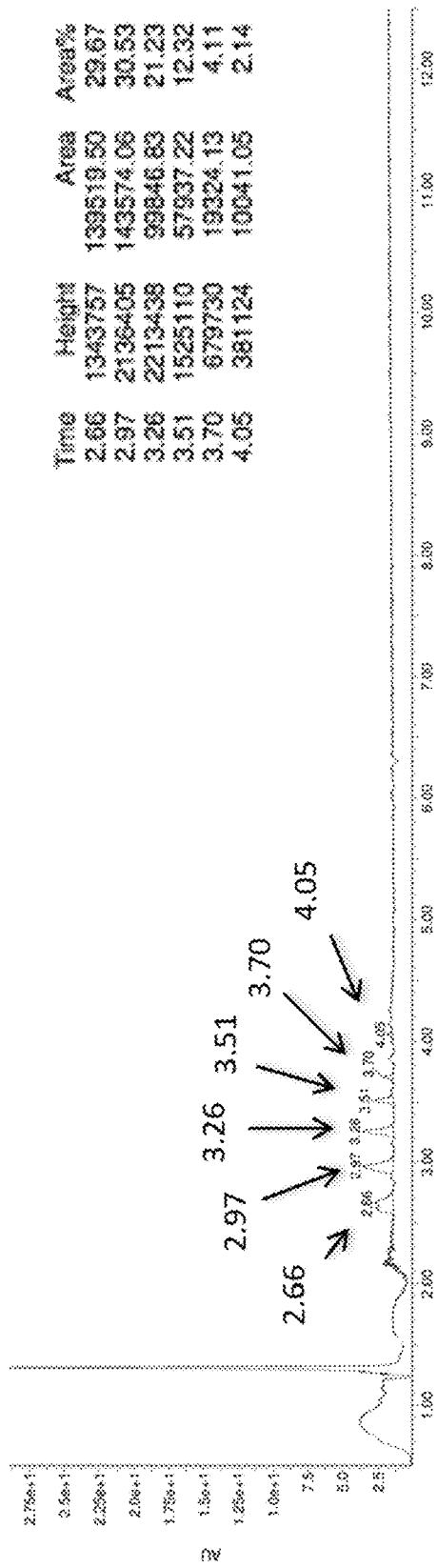
FIG. 14. MALDI and mass spectrometry analysis.
Figure 14:
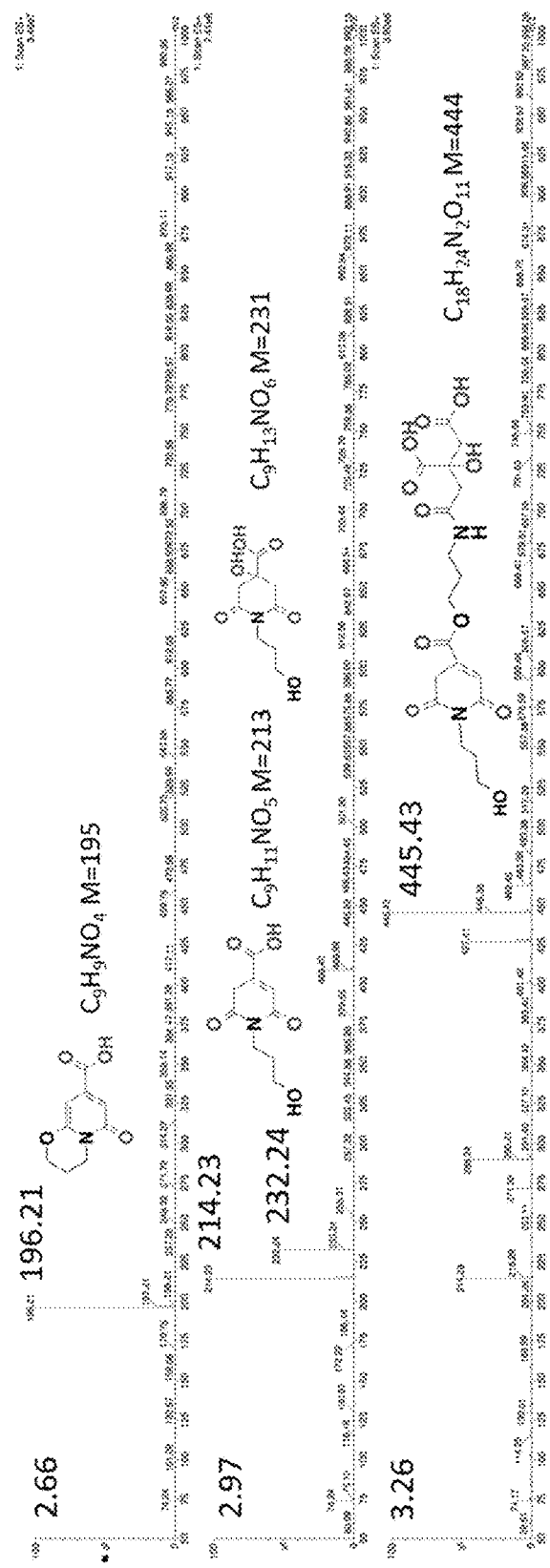

To identify the chromophore structure in the oligomer, representative compounds of the decomposition products of panthenol, pantolactone and β-alanol were also reacted with citric acid under the same condition (120° C. for 2 hours). Chemical characterization showed citric acid was first reacted with the amide of panthenol and dehydrated to form a six-membered ring after imide formation. 3-amino-1-propanol was reacted with citric acid to further characterize the reaction that occurs for chromophore formation. 1H and COSY NMR spectra confirmed the unique proton peak of dehydrated citric acid at 2.2 ppm (assigned as 7) due to conjugated electrons that resulted in the chemical shift of citric acid (2.5-2.7 ppm) as shown in FIG. 2. The split peaks at 1531 cm-1 of N—H and N—O, and decreased peak at 1647 cm-1 of C=O in amide bonds, as well as the new peak of imide bonds at 1780 cm-1 in the ATR FTIR spectra show that carboxylic groups reacted with amide bonds and adjacent hydroxyl groups of panthenol. Panthenol citrate (PAN-CA) showed the characteristic peak of C=C stretching at 1703 cm-1 that is in the same position with itaconic acid in PAN-IA, PAN-IA-CA and PAN-IA-CA-PEG. This indicates the formation of double bonds between panthenol and citric acid, suggesting the presence of a new structure. The chromophore, 6-oxo-3,4-dihydo-2H, 6H-pyrido(2,1-b]oxazine-8-carboxylic acid, is 196.21 Da observed in HPLC-ESI MS spectra with exact mass at 195 Da, meanwhile multiple peaks in 214, 232, 445 and 659 m/z again demonstrated the dehydration of citric acid and the imide ring formation of panthenol citrate, indicating that panthenol is decomposed to β-alanol and pantoic acid in the acidic condition or in the presence of citric acid and β-alanol further reacts with citric acid to from the chromophores that are attached to 6-oxo-3,4-dihydro-2H,6H-pyrido(2,1-b]oxazine-8-carboxylic acid (FIG. 14). MALDI and MS data showed the chromophores are oligomers with very low molecular weight, and stable as hydrolysis of panthenol citrate oligomers in NaOH solution did not change the excitation and emission wavelength of fluorescence.

Figure 3:
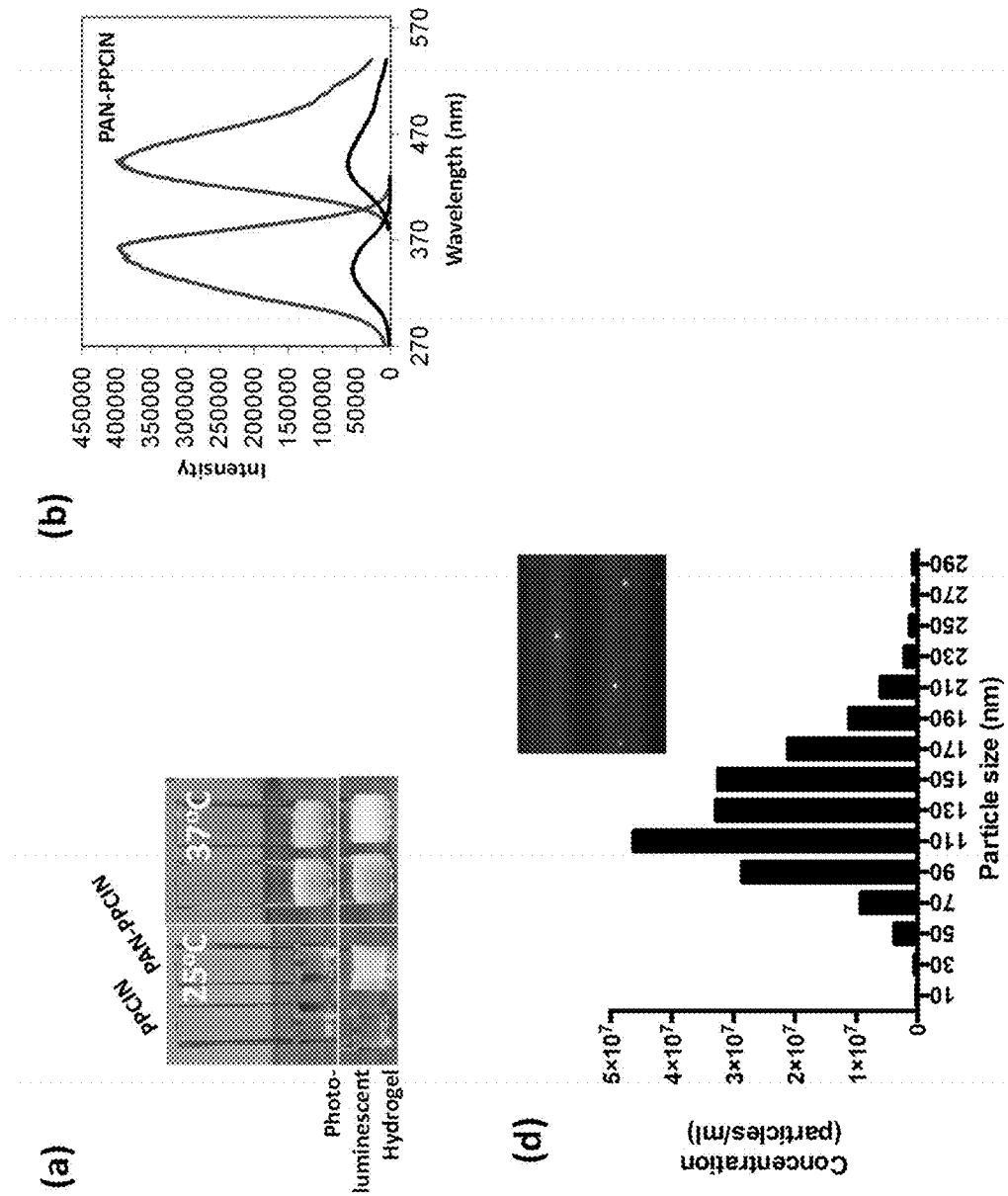
FIGS. 3A-E. (a) Gross images of phase transition of PPCIN and photoluminescent PAN-PPCIN hydrogel in 25° C. and 37° C. with and without UVA radiation. (b) Excitation and emission intensities of photoluminescent PAN-PPCIN hydrogel in 100 mg/ml (red) and 10 mg/ml (black). (c) Low critical solution temperatures of PPCIN and PAN-PPCIN hydrogel (100 mg/ml, pH=7.4) measured via circular dichroism spectrophotometry. (d) Particle size and image of PAN-PPCIN (2 mg/ml, pH=7.4) at room temperature (e) Storage modulus (G') and loss modulus (G") changes of PPCIN and PAN-PPCIN hydrogels (100 mg/ml, pH=7.4) as a function of temperature.
Figure 3:
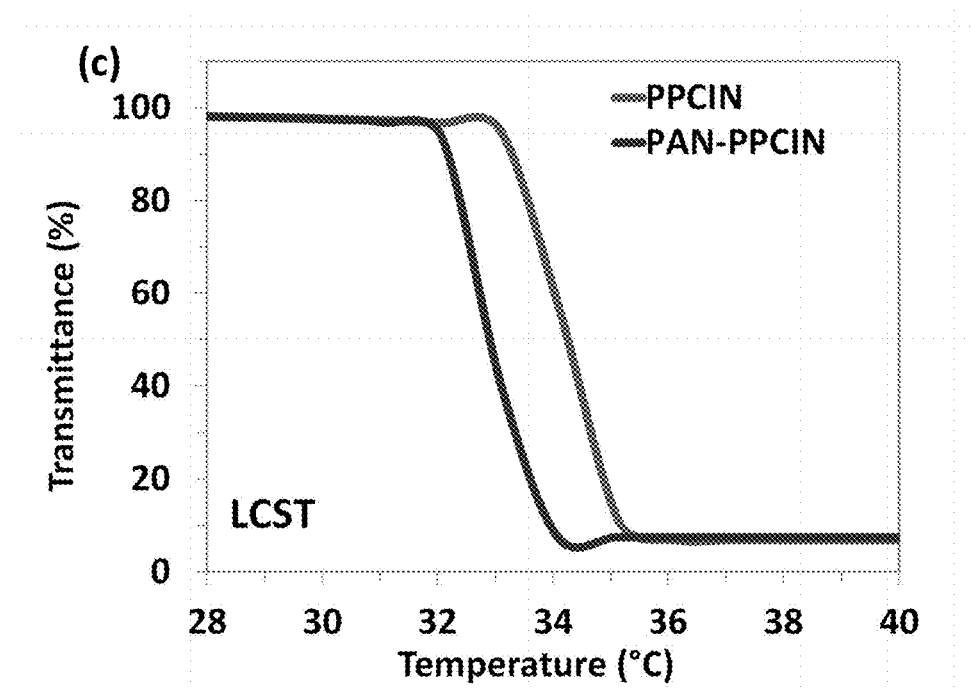
Figure 3:
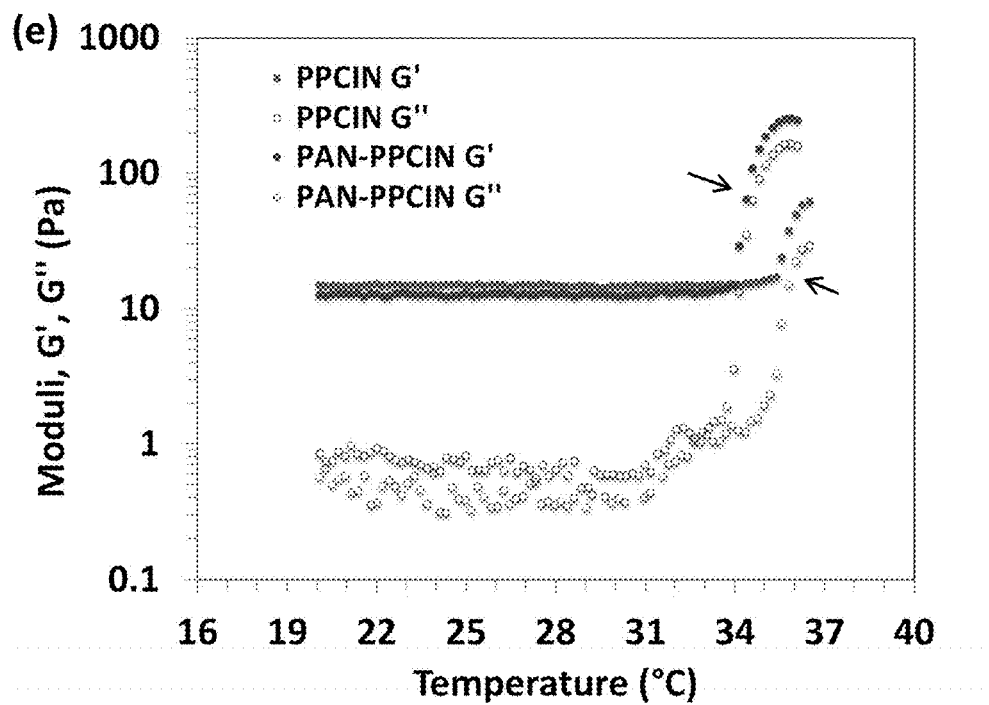

To demonstrate the ability to synthesize biomaterials from these oligochromophores, photoluminsecent thermoresponsive gels and elastomers were synthesized and characterized. Thermoresponsive photoluminsescent hydrogels were synthesized by reacting the condensation product of citric acid, panthenol, polyethylene glycol and itaconic acid (PAN-CA-IA-PEG) with N-isopropylacrylamide via free radical to form PAN-PPCIN. The lower critical solution temperature (LCST) for PAN-PPCIN (100 mg/ml, pH=7.4) was 33° C. and the excitation and emission wavelengths of the gel did no change (FIG. 3), while intensities showed the concentration dependence. The storage and loss moduli for PAN-PPCIN and PPCIN at room temperature were 12.7±0.3 MPa and 14.9±0.2 MPa and 0.72±0.1 MPa and 0.42±0.08 MPa, respectively. At low oligomer concentrations (<40 mg/ml), these materials form nanoparticles via self-assembly at room temperature with particle size distribution of 90 nm to 170 nm.

Figure 4:
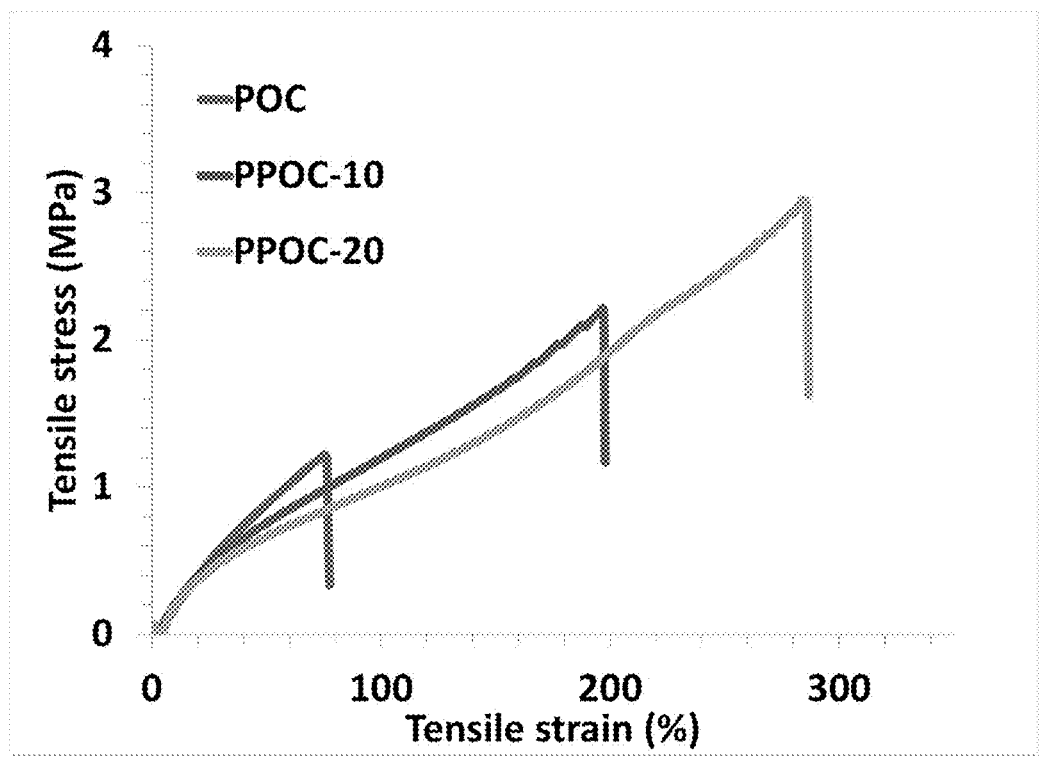
FIGS. 4A-B. (a) Photoluminescent image and mechanical measurement of POC and PPOC with 10 mol % panthenol (PPOC-10) and 20 mol % panthenol (PPOC-20), including tensile strength (MPa), Young's modulus (MPa) and stress-strain curves. (b) Cummulative in vitro release curves of panthenol from PPOC, calculated by calibration curve (left).
Figure 4:
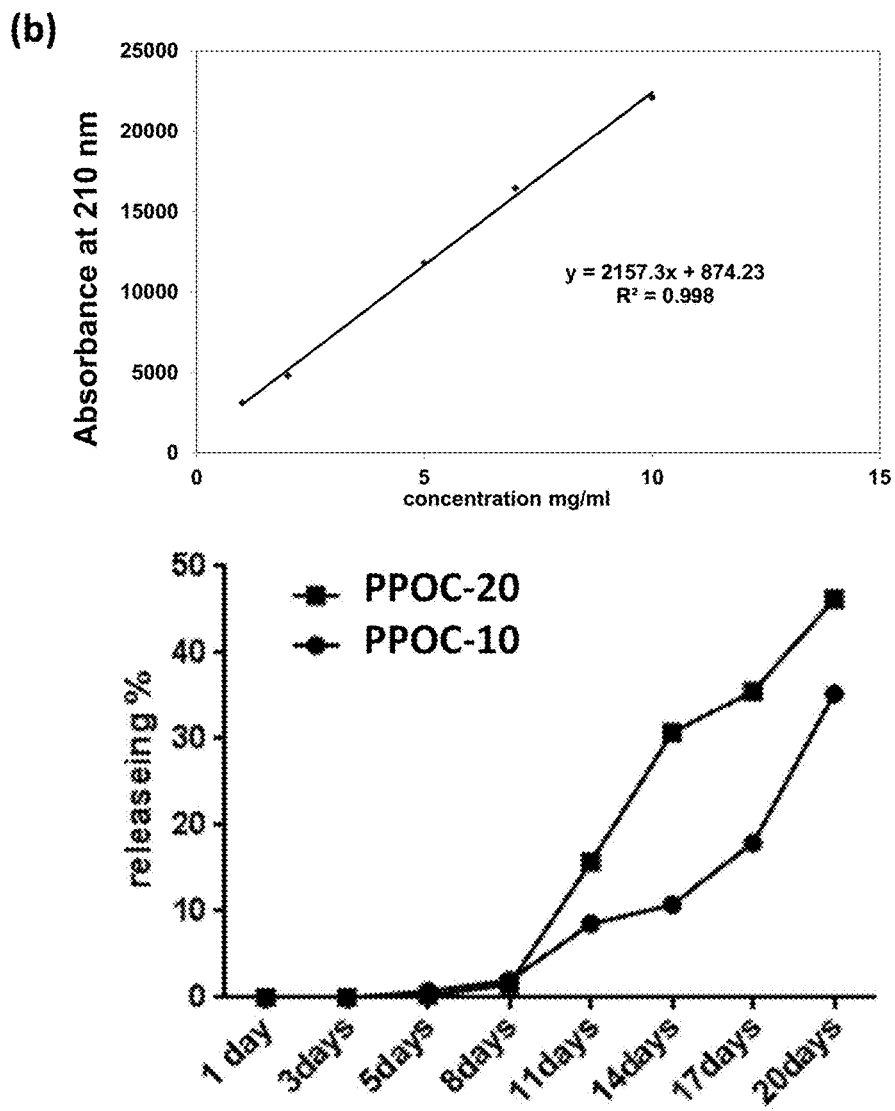

Panthenol citrate-based elastomers were also synthesized. Elastomers were synthesized by the condensation polymerization of 1,8-octanediol, panthenol, and citric acid at 60° C. for 5 days. These PPOC elastomers were photoluminescent with excitation at 350 nm and emission at 440 nm. Tensile strength, Young's modulus and elongation-at-break of panthenol citrate elastomers increased significantly with the incorporation of panthenol when compared to poly(1,8 octanediol citrate) (POC) (FIG. 4). A small amount of panthenol resulted in tensile strength and Young's modulus of 2.52±0.29 MPa and 3.03±0.38 MPa, respectively, double the values of the strength and modulus of POC synthesized under the same reaction condition. Photoluminescent elastomers were also successfully synthesized by post-polymerizing the prepolymer of poly(1,8 octanediol citrate) in the presence of panthenol. Panthenol can effectively increase the elasticities and flexibilities of polydiolcitrate elastomers. Using this method, the structure of panthenol is better preserved and we observe slow release of panthenol over time from the elastomer.

Figure 5:
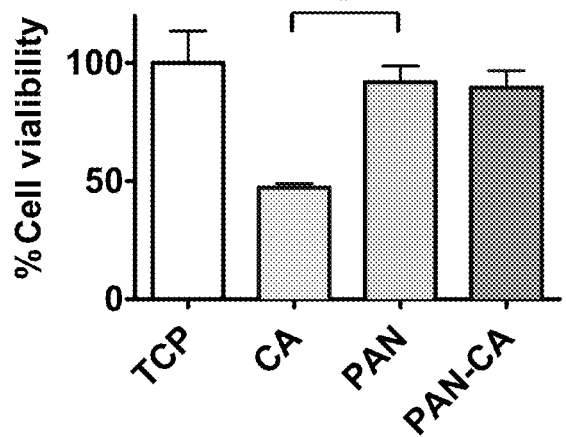
FIGS. 5A-G. (a) Quantitative analysis of live/dead cell viability of HUVEC cells cultured with panthenol citrate oligomers (1.0 mg/ml), 5.2 mM citric acid and 4.88 mM panthenol. (b) Microscopy images of HEKa cells cultured on (TCP) and with UV exposure (UV 60 min) in the treatment of panthenol citrate (1 mg/ml), including phase (left), DHE fluorescence (middle) and merged images (right). (c) Quantitative analysis of DHE fluorescent intensities in keratinocytes with and without panthenol citrate treatment under UV exposure. (d) ATBS scavenging of panthenol (PAN), panthenol citrate (PanCit) that shows free radical inhibition of panthenol citrate, compared to panthenol. (e) Fluorescence intensities of panthenol citrate (0.1 mg/ml) quenched by free radical TEMPO from 0.001 M to 0.2 M over time, excited at 365 nm. (f) Fluorescence intensities of panthenol citrate (0.1 mg/ml) quenched by ROS generated by $Fe^{2+}$, $H_2O_2$, Ascorbic acid and EDTA over time, excited at 365 nm. (g) Fluorescence intensities of partially oxidized panthenol citrate (0.1 mg/ml) by ROS.
Figure 5:
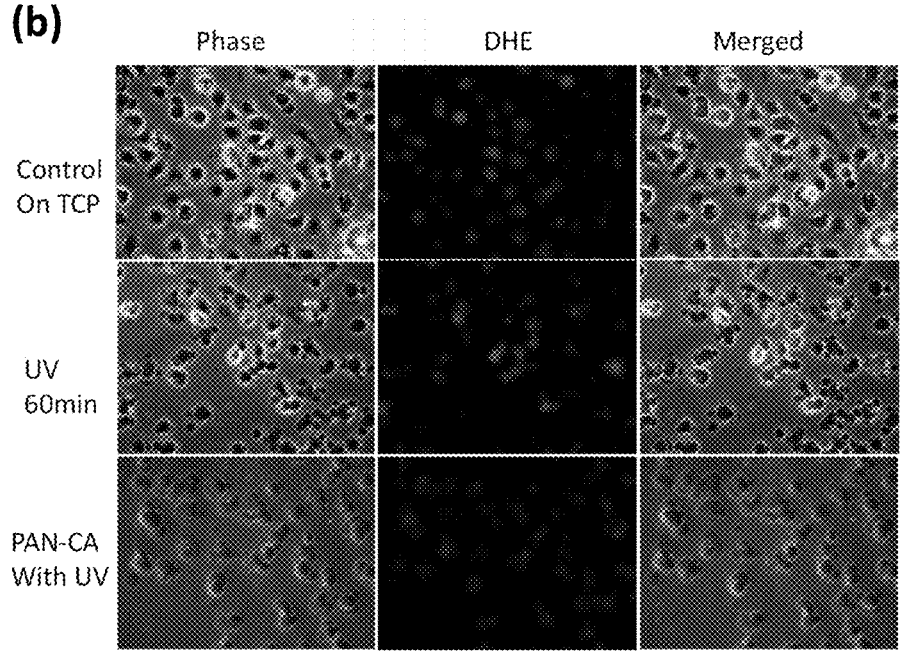
Figure 5:
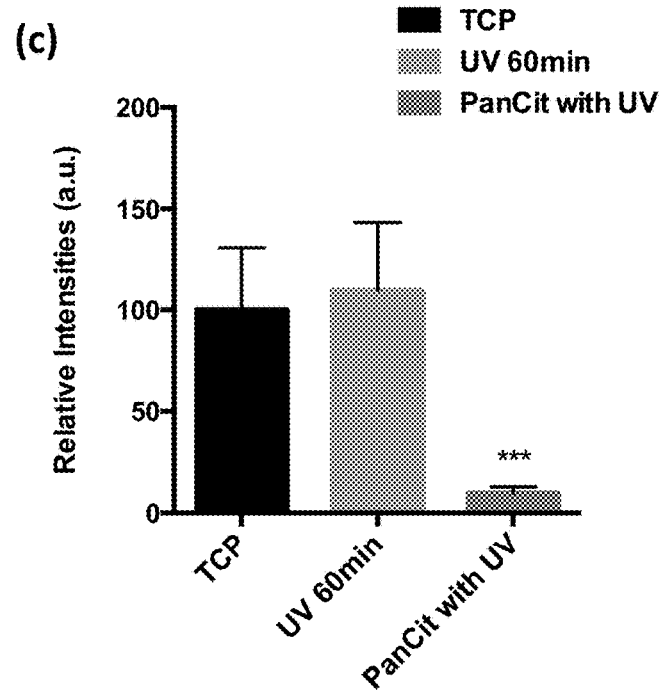
Figure 5:
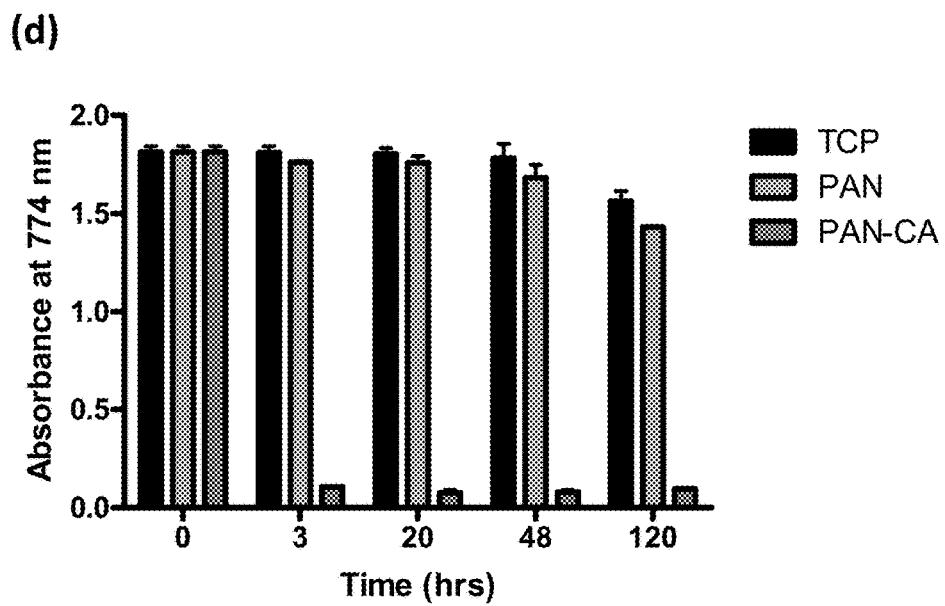
Figure 5:
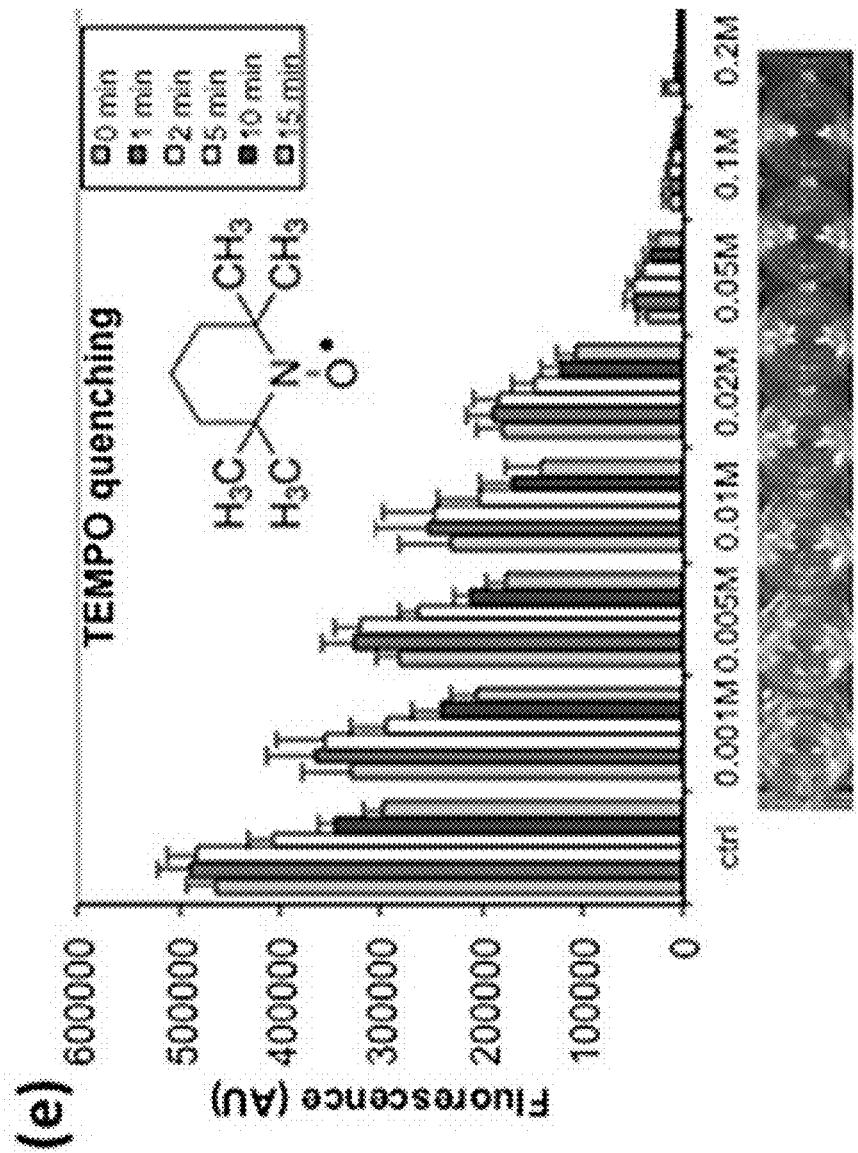
Figure 5:
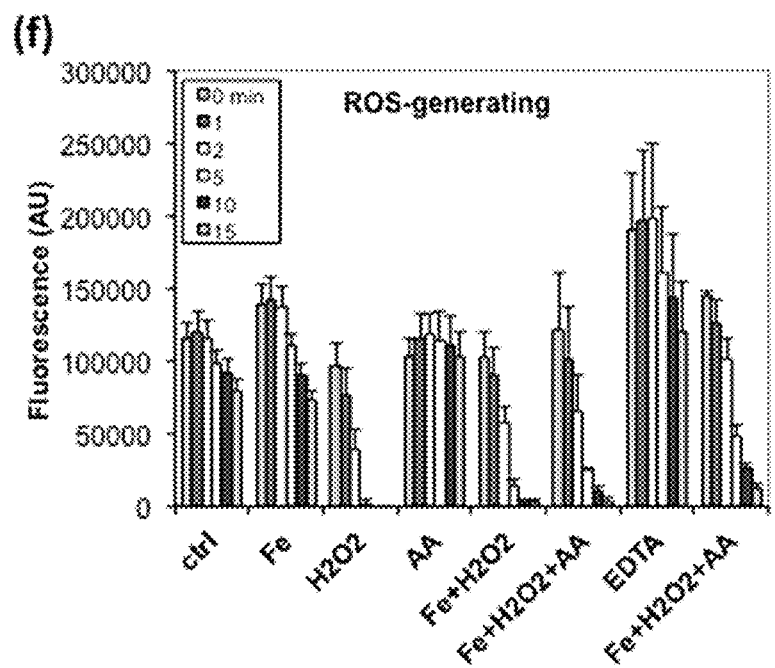
Figure 5:
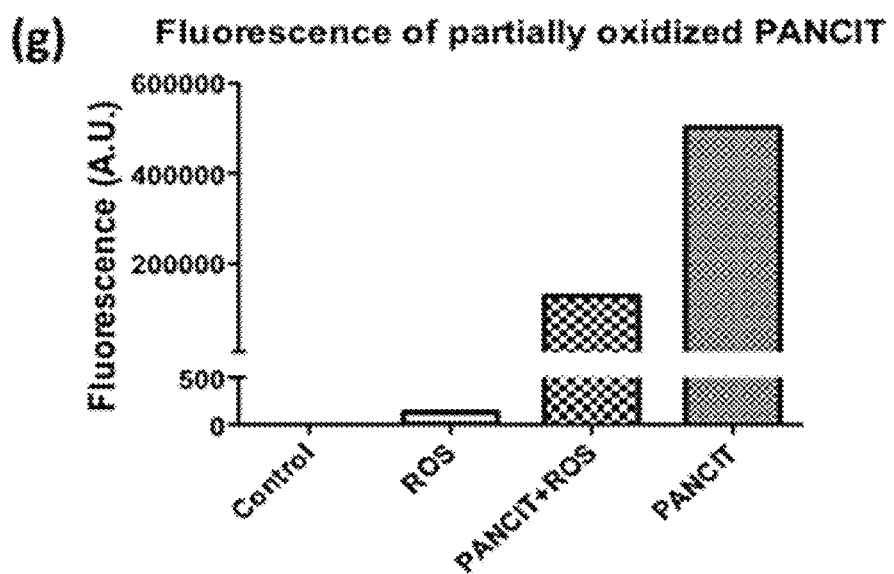
Figure 6:
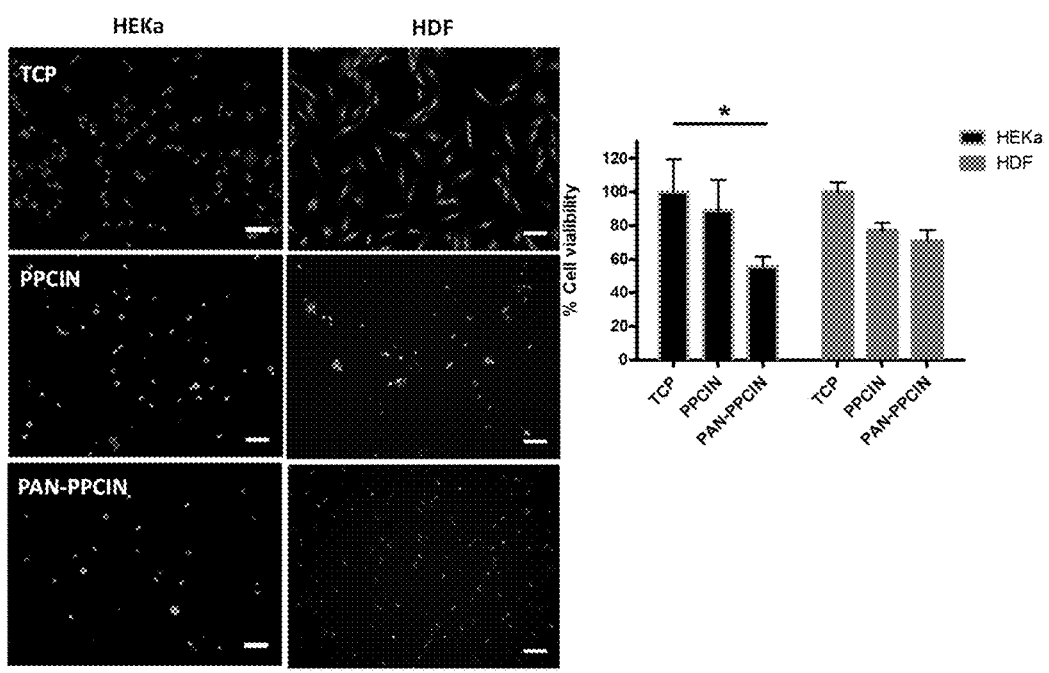
FIG. 6. Merged fluorescent images of HEKa and HDF cells cultured with PPCIN and PAN-PPCIN hydrogel (100 mg/ml, pH=7.4). The cells were stained with calcein AM and Ethidium homodimer-1, the scalar bar is 100 um. Quantitative analysis of live/dead cell viability of cells cultured with different panthenol citrate oligomers.
Figure 7:
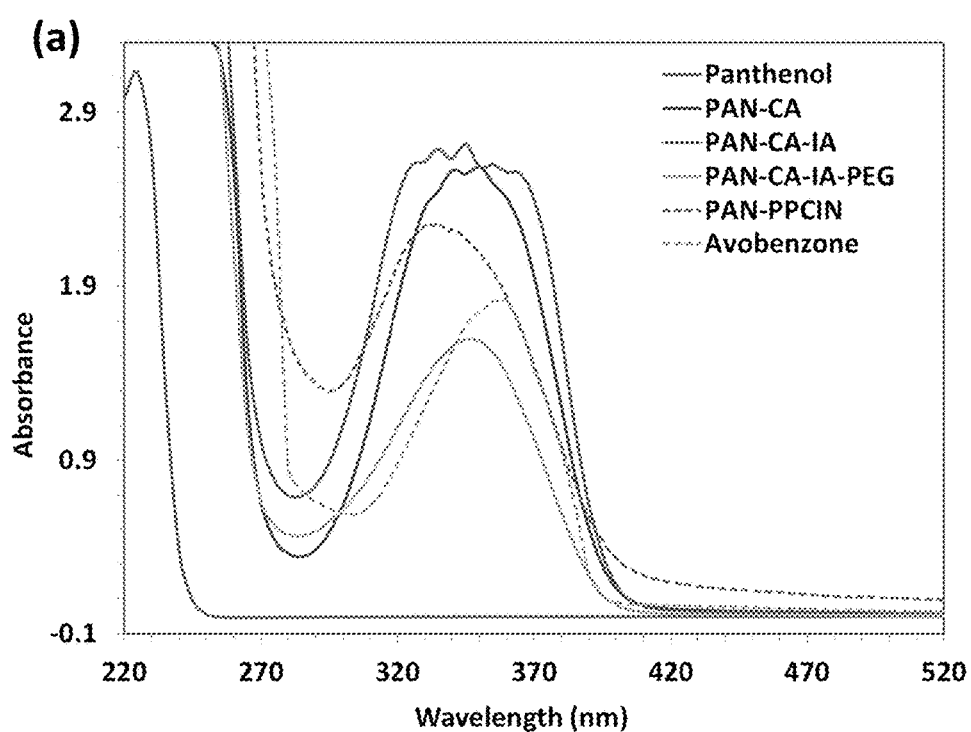
FIG. 7A-C. (a) UV/Vis spectra of panthenol citrate oligomers in water at 25° C. with the same concentration of 10 mg/ml, including PAN-CA (1:1), PAN-CA-IA (1:0.8:0.2) and PAN-CA-IA-PEG (0.5:0.8:0.2:0.5), as well as that of PAN-PPCIN hydrogel with 50 mol % panthenol in 100 mg/ml concentratrion, panthenol and avobenzone as a comparison. (b) Endothermic phase transitions of PPCIN and PAN-PPCIN hydrogel (100 mg/ml, pH=7.4) over time under 365 nm UVA radiation from top to bottom, PAN-PPCIN was photoluminescent from 0 to 120 seconds. (c) UVA radiation of pig skins covered by 500 ul PPCIN and PAN-PPCIN hydrogel (100 mg/ml, pH=7.4) for 15 minutes, and H&E staining of irradiant pig skins, scale bar is 100 um.
Figure 7:
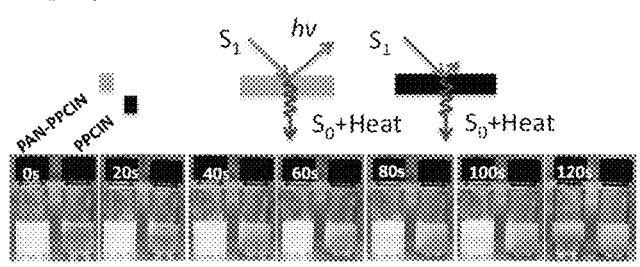
Figure 7:
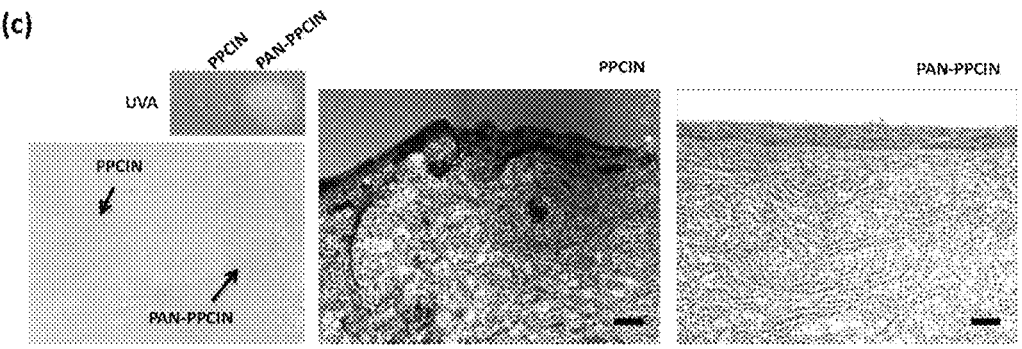

The cytotoxicity of panthenol citrate was evaluated using human umbilical vein endothelial cells (HUVECs), adult human epidermal keratinocytes (HEKa) and human dermal fibroblasts (HDF). In particular, the following samples were evaluated: (1) panthenol, (2) citric acid, (3) panthenol citrate. There was no toxicity observed for all three cell types at low doses (<0.1 mg/ml). At higher concentrations (1 mg/ml), HUVEC cells treated with citric acid, died within 24 hours while there was no significant difference between cells exposed to panthenol and panthenol citrate (FIG. 5), HDF cell proliferation was inhibited when treated at higher concentrations of citric acid and panthenol citrate (>1 mg/ml). Viability of both HUVEC and HEKa cells decreased to 50% at higher doses of panthenol citrate (>3 mg/ml). Similarly, in vitro cytocompatibility of PPCIN and PAN-PPCIN thermoresponsive hydrogels were evaluated by culturing with HEKa and HDF cells. The cells were round and aggregated inside the hydrogels with incubation time. Live/Dead assay showed both types of cells survived in PPCIN hydrogel for 24 hours. However, cell viability decreased in PAN-PPCIN hydrogel synthesized at 10 mol % panthenol. Due to degradation of PAN-PPCIN hydrogel, the released panthenol citrate in higher concentration may have caused the decrease in cell viability. Compared to HEKa cells in PPCIN hydrogel, HDF cells were more viable at 24 hours. UVA radiation can generate oxidative stress in the mitochrondia of keratinocytes. 1 mg/ml panthenol citrate can effectively suppress the generation of superoxide. Both panthenol citrate and PAN-PPCIN with panthenol citrate can scanvenge radicals as per the ABTS assay results.

Panthenol citrate oligomers and thermoresponsive hydrogels show strong ultraviolet absorption at 350 nm. Panthenol and citric acid must be in the oligomer composition of this phenomenon to be observed. Ultraviolet absorption for both panthenol-substituted polymers was increased with increasing content of panthenol and broader than those of commercially available products such as avobenzone and zinc oxide. The maximum absorbance of panthenol citrate oligomers is adjustable by incorporating itaconic acid and/or polyethylene glycol. Both PPCIN and PAN-PPCIN hydrogel (100 mg/ml pH=7.4) can perform endothermic phase changes under direct exposure in 365 nm wavelength UVA radiation, however PAN-PPCIN hydrogel shows a delayed phase transition at 120 seconds due to fluorescent emission. Photoluminescent hydrogels likely reflected UV irradiance and decreased photothermal conversion efficiency minimizing UV burn damage. Compared to naked skin under UVA radiation, both PPCIN and PAN-PPCIN hydrogels reduced changes in the skin after exposure to UVA and UVB.

Example 3

Synthesis and Mechanical Characterization of Poly(Panthenol Citrate-Co-e-Caprolactone)

Figure 8:
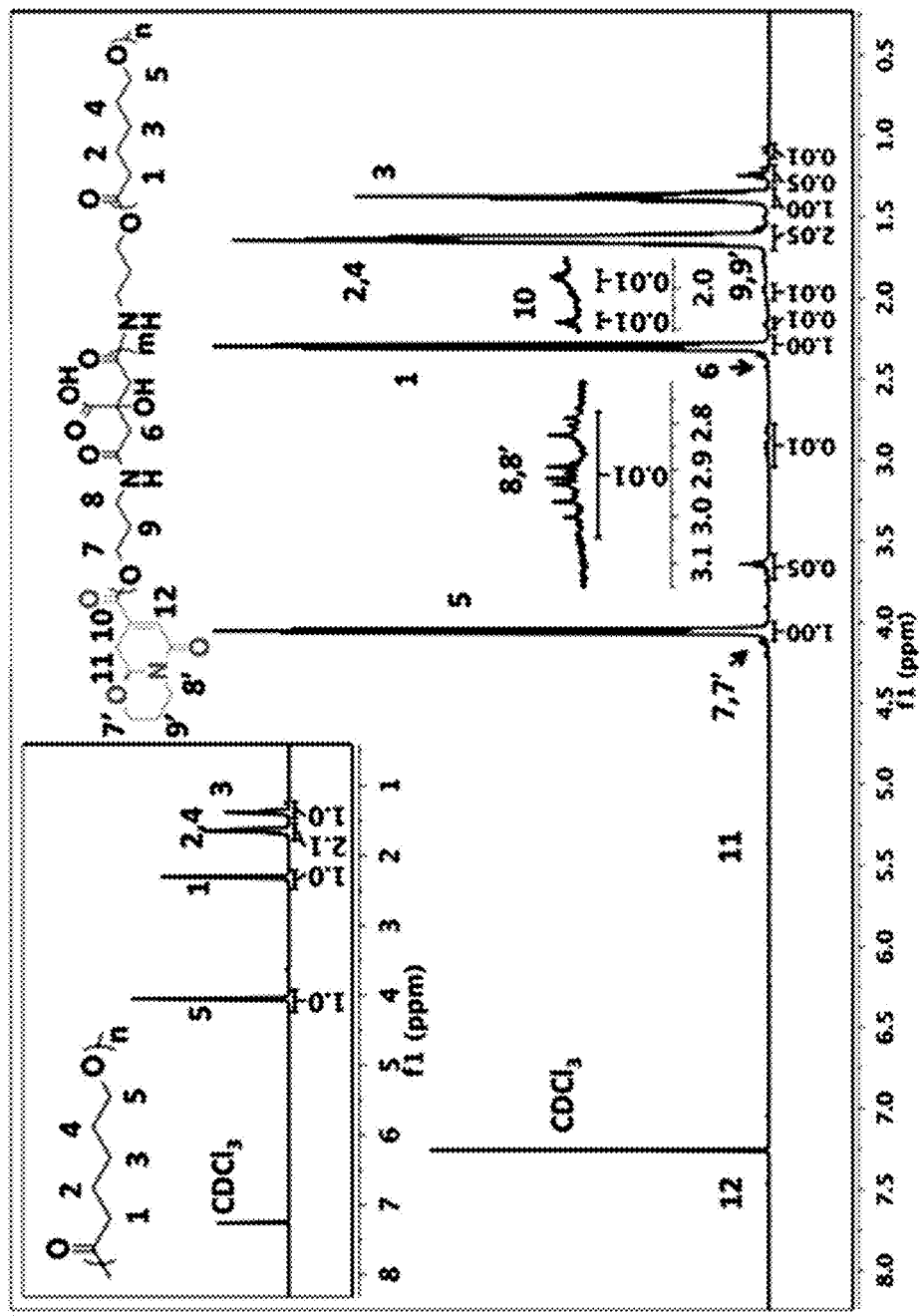
FIG. 8. $^1$H NMR spectra of poly(ε-caprolactone) (insert) and poly(panthenol citrate-co-ε-caprolactone) copolymer in CDCl$_3$.

Poly(panthenol citrate-co-e-caprolactone) copolymer (PanCit-PCL) was synthesized by enzyme catalyzed ring opening polymerization at 60° C. using panthenol citrate as macroinitiators. Briefly, freeze-dried panthenol citrate (0.002 mol) and e-caprolactone (0.1 mol) were added into a 50 ml flask and mixed well, lipase acrylic resin from Candida Antarctica were added to the flask with a percentage of 10 wt % to e-caprolactone. The reaction was performed in a vacuum for 5 days. The copolymer was dissolved in dimethylene chloride and lipase acrylic resin was removed by a filter paper, precipitated in ethanol and washed by pure water before freeze drying. Poly(e-caprolactone) homopolymer (PCL) was also synthesized at the same procedure as a reference material. $^1$H and COSY spectra of poly(panthenol citrate-co-e-caprolactone) copolymer was recorded using a Ag500 NMR spectrometer (Bruker, Billerica, Mass.) at ambient temperature, using CDCl$_3$ as solvent and tetramethylsilane (TMS) as an internal reference (FIG. 8). The number average molecular weight Mn was determined using gel permeation chromatography (GPC) (Agilent 1100 series equipped with Brookhaven BI-DNDC differential refractometer and BI-MwA Light scattering detector). GPC consisted of an Agilent G1310A pump and a PLgel 10 um Mixed-B LS column. Monodisperse polystyrene (PS) standards with five number-averaged molecular weights (4000, 13700, 19300, 44000, 500000 Da) were used to obtain an internal calibration curve. The dn/dc value used for PS in DMF was 0.1615 mL/g, and the dn/dc of DMF was 1.431 mL/g. All the standards and samples were dissolved to 10 mg/mL in DMF with 10 mM LiBr as mobile phase at a rate of 1.0 ml/min, injection volume of 100 µL and measurements were taken at 25° C. (620 nm). Poly(panthenol citrate-co-e-caprolactone) copolymer and poly(e-caprolactone) homopolymer were processed into round discs (7.1 mm×3.25 mm, Height×Diameter), and compression test was performed at a the cross head speed was set at 10 mm/min.

Antioxidant Properties and Fluorescence Quenching

The iron chelation activity was assessed by incubating samples (100 mg for solid polymers PCL, PanCit-PCL, PDC, PanCit-PDC and PanCit) with 0.25 mM FeCl$_2$.4H$_2$O solution (50 mg/mL) at 37° C., blank without polymer were used as a negative control. Supernatants were collected at each time point and reacted with 5 mM ferrozine indicator solution in a 5:1 ratio. Ferrous ions chelated by polymers will not be available for ferrozine reaction, resulting in lower color development. Absorbance was measured at 534 nm and the percentage of iron chelated calculated.

The antioxidant activity of polymers was also evaluated using the β-carotene-linoleic acid assay with a few modifications as described below. 64 Briefly, tween 40 (4 g), β-carotene (4 mg) and 0.5 mL linoleic acid were mixed in 20 mL chloroform. After removing chloroform in a rotary evaporator, 30 mL of pre-warmed Britton buffer (100 mM, pH 6.5) was added to 1 mL of the oily residue with vigorous stirring. Aliquots (1 mL) of the obtained emulsion were added to the samples (100 mg for solid polymers PCL, PanCit-PCL, PDC, PanCit-PDC and PanCit), blank without polymer were used as a negative control. Reaction mixtures were incubated at 45° C. for 100 minutes. Spontaneous oxidation of linoleic acid at 45° C. leads to β-carotene discoloration, which was monitored by the decrease in absorbance at 470 nm, starting immediately after sample preparation (t=0 min).

Photoluminescent Panthenol citrate oligomer can be incorporated into the macromolecular chain of biodegradable poly(ε-caprolactone) via ring opening polymerization in the presence of lipase (FIG. 8), the resulted poly(panthenol citrate-co-ε-caprolactone) copolymer has a lower molecular weight of 21998.9 Da and a boarder polydispersity Index of 1.98 compared to poly(ε-caprolactone) homopolymer (25531.7 Da and 1.51) due to end group initiation of panthenol citrate macroinitators. Under ultraviolet light at 365 nm, PanCit-PCL emits blue light (FIG. 9a) and shows higher compression strength at maximum.

Figure 9:
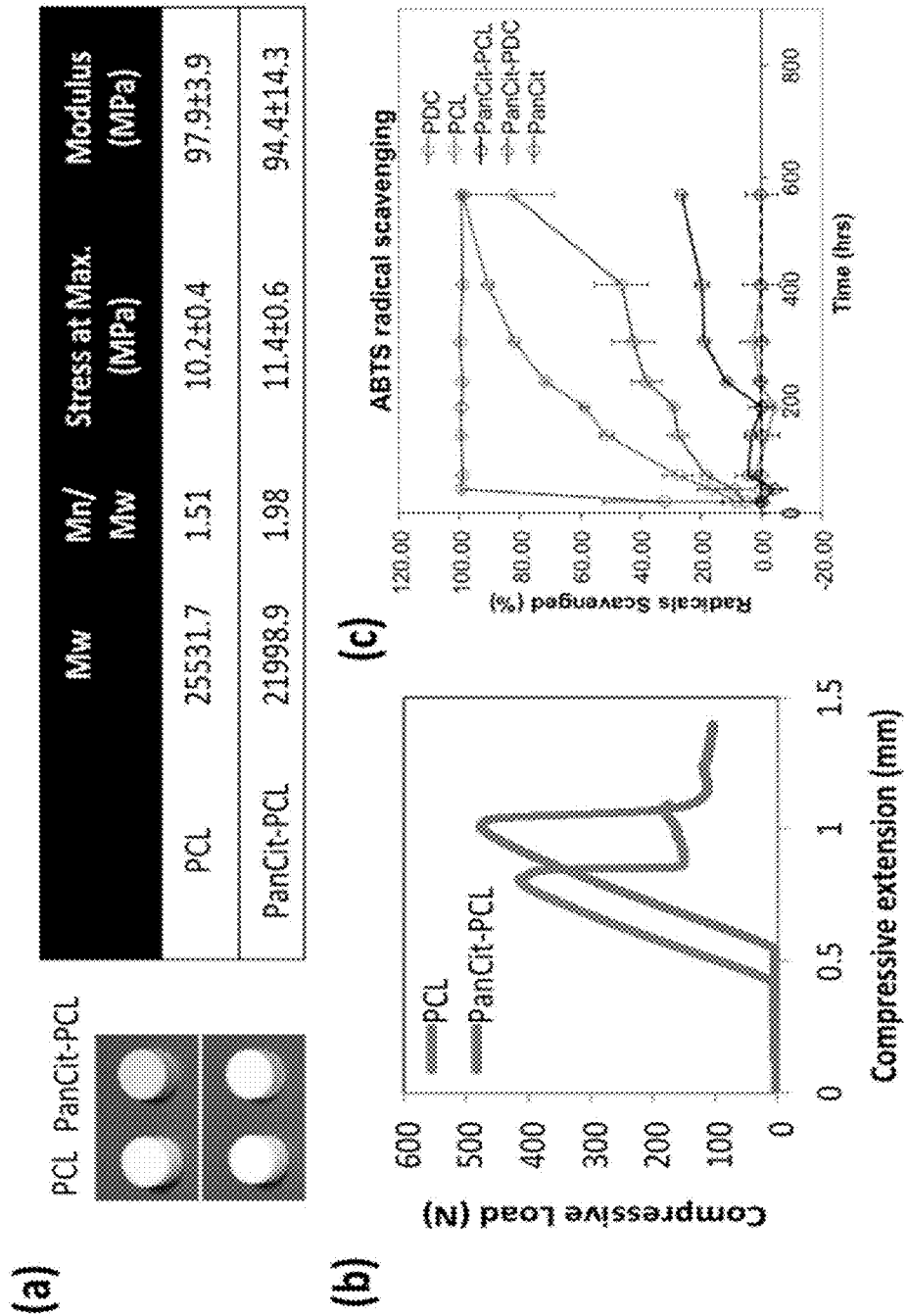
FIGS. 9A-E. (a) Photoluminescent images, molecular weight and its distribution, mechanical measurement of PCL and PanCit-PCL, including the compressive stress at maximum (MPa) and compressive modulus (MPa); (b) compressive load-extension curves of PCL and PanCit-PCL discs. (c) ATBS scavenging of PDC, PanCit-PDC, PCL, PanCit-PCL and PanCit, blank as a control; (d) Iron chelation capacity of PDC, PanCit-PDC, PCL, PanCit-PCL and PanCit; (e) Inhibition of lipid peroxidation of PDC, PanCit-PDC, PCL, PanCit-PCL and PanCit.
Figure 9:
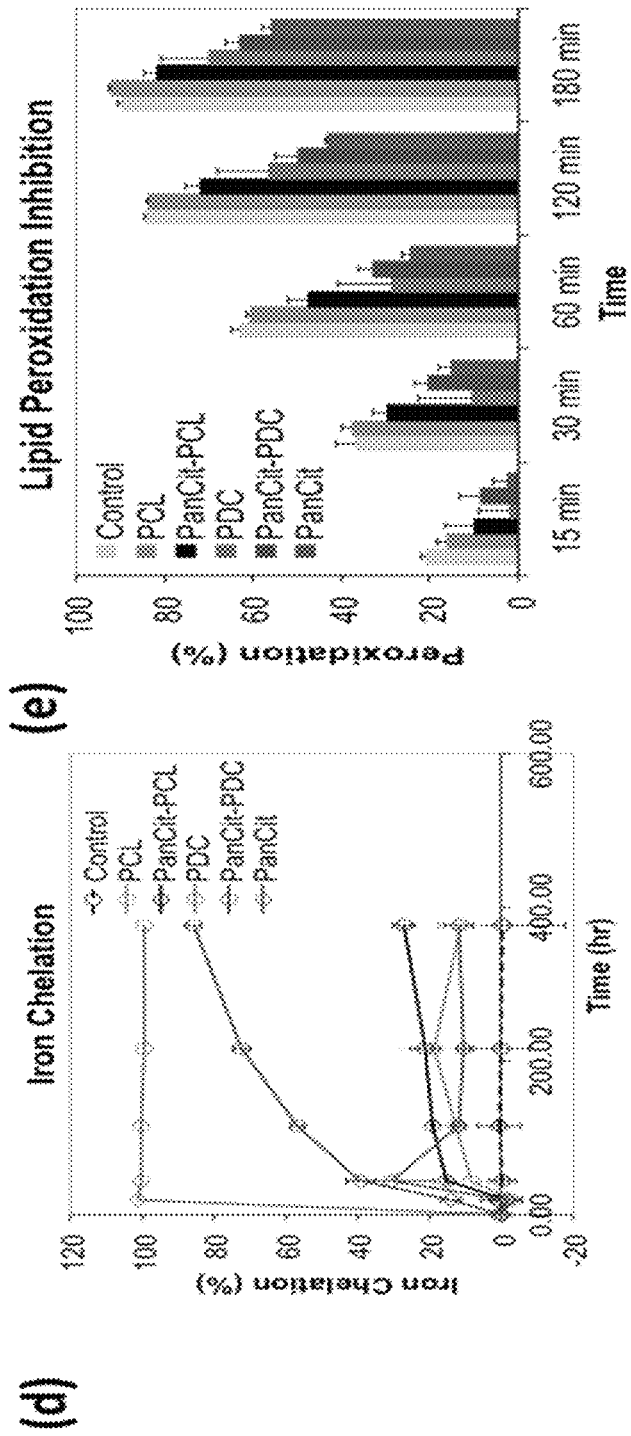

As shown 100% free radical scavenging in 24 hours in FIG. 9c, panthenol citrate has an excellent radical scavenging capability and inhibit lipid peroxidation, consequently it enhances poly(ε-caprolactone) in the radical scavenging and lipid peroxidation inhibition after incorporation. As reported (van Lith, R., et al. Biomaterials, 2014. 35(28): p. 8113-22; herein incorporated by reference in its entirety), Poly(diol citrate)s (PDC) show significant antioxidant capacity which is affected by the incorporation of panthenol citrate, unlike the rapid 100% iron chelation of PDC in 24 hours, iron chelation of PanCit-PDC increases gradually in a long term. Similarly, the fluorescence of panthenol citrate was quenched by free radical and reactive oxygen species in FIGS. 5e and 5f, the chromophore, 6-oxo-3,4-dihydo-2H, 6H-pyrido(2,1-b]oxazine-8-carboxylic acid, showed the correlation of fluorescence and radicals. However, the fluorescence of partially oxidized panthenol citrate quenched by ROS indicated panthenol citrate backbone without chromophore also contribute to the antioxidant properties.

Example 4

Antioxidant Properties of PanCit

Equimolar amounts of panthenol and citric acid (1:1) were reacted (120° C., vacuum, 2 hrs) and purified by precipitation in ethanol followed by vacuum drying. Radical scavenging ability was measured by absorption decay using the ABTS assay at 734 nm (50 mg/mL polymer), inhibition of lipid peroxidation by absorbance retention at 470 nm of beta-carotene bleaching assay (50 mg/mL polymer), and cell protection from oxidative stress by treating human umbilical vein endothelial cells with PanCit (1 mg/mL) and then exposing cells to $H_2O_2$ (200 uM, 1 hr), after which dihydroethidium (DHE, 10 uM, 1 hr) was added and fluorescence recorded.

Figure 10:
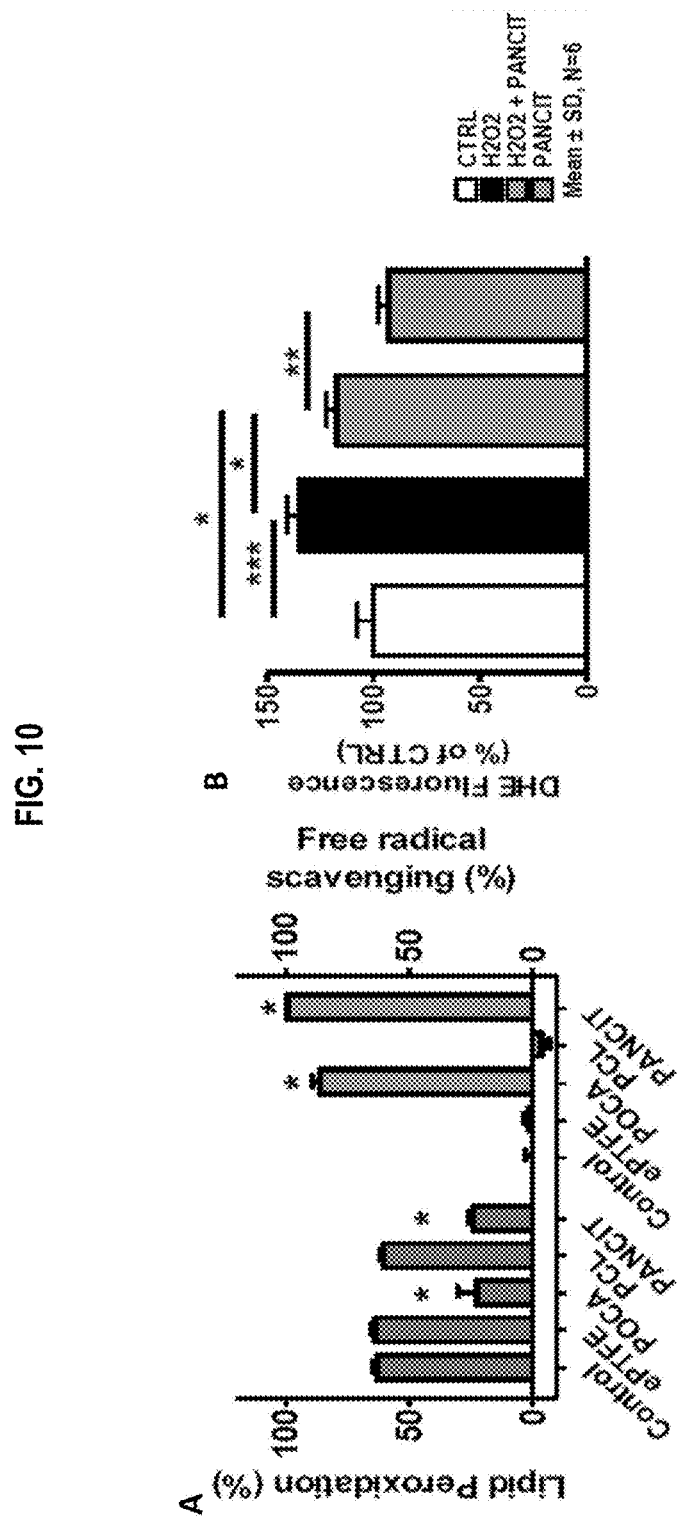
FIGS. 10A-B. (A). PANCIT scavenges free radicals and inhibits lipid peroxidationas assessed using ABTS and beta-carotene bleaching assay similar to ascorbic acid containing polymer (POCA). N=3, Mean+SD, *p<0.05. B. H$_2$O$_2$ increases ROS in human umbilical vein endothelial cells (HUVECs), which can be inhibited by PANCIT.

PanCit scavenged free radicals and inhibited the peroxidation of lipids in a similarly to ascorbic acid-containing polydiolcitrates POCA (van Lith et al. Biomaterials, 2014). Control polymers used in medical devices such as polycaprolactone (PCL) and expanded polytetrafluoreoethylene (ePTFE) do not exhibit any antioxidant capacity (FIG. 10A). Endothelial cells exposed to hydrogen peroxide show an increased level of reactive oxygen species as assessed using DHE fluorescence, are suppressed by PANCIT, indicating the ability of PanCit to have functional antioxidant effects on living cells (FIG. 10B).

Example 5

Engineered PanCit to Emit a Fluorescence Signal that is Proportional to Antioxidant Capacity Fluorescent intensity of the oligomers in pure form or in aqueous solution (10 mg/ml) was recorded at 440 nm for emission excited at 350 nm and 365 nm, respectively. Fluorescence intensity of PanCit solutions (2 mg/mL in MQ water) was recorded and quantified using a UVP EpiChemi II bio-imaging darkroom using LabWorks software. Lipid peroxidation inhibition capacity was assessed.

Figure 11:
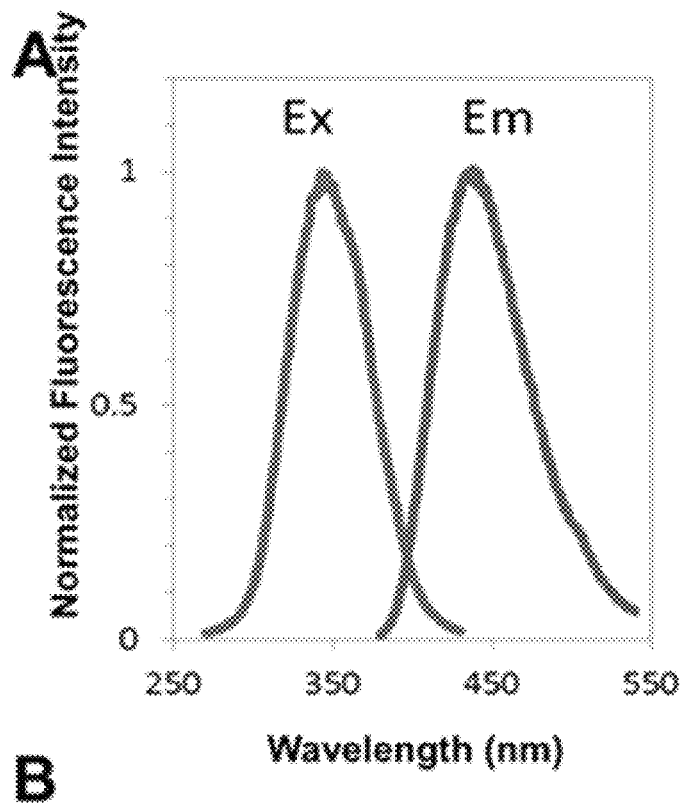
FIGS. 11A-D. Polydiolcitrates exhibit fluorescence and antioxidant properties. (A) Emission and excitation wavelength for PanCit. (B) PanCit confers fluorescent properties to elastomeric polydiolcitrates when combined with aliphatic diols. Example shown is combination with poly(1,8 octanediol citrate) (POC). (C) Fluorescence intensity signals from PanCit samples that were or were not exposed to reactive oxygen species. Decreased fluorescence signal from PanCit that was exposed to ROS, indicating correlation of fluorescence with antioxidant properties. (D) Lipid peroxidation inhibition using PanCit that was or was not exposed to ROS. Reduction of the inhibitory capacity of PanCit after exposure to ROS indicates the reduced antioxidant capacity after ROS exposure.
Figure 11:
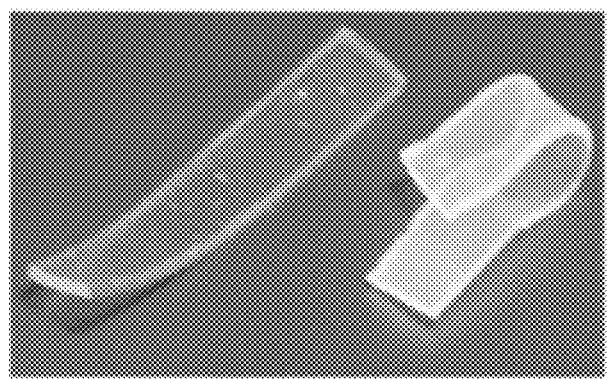
Figure 11:
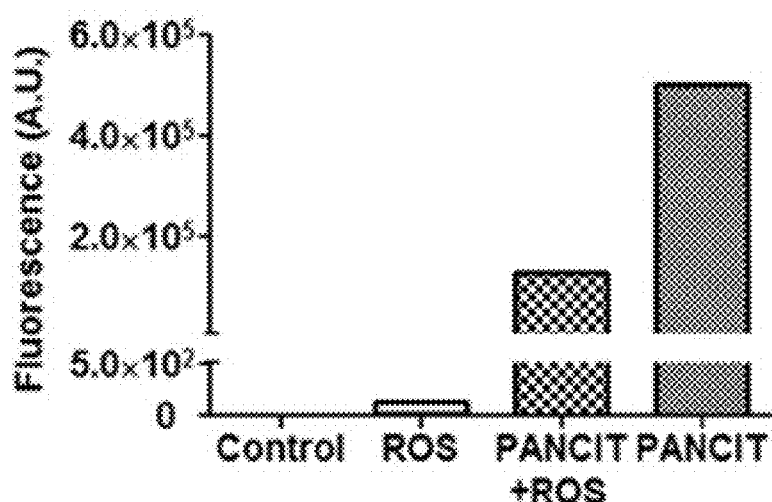
Figure 11:
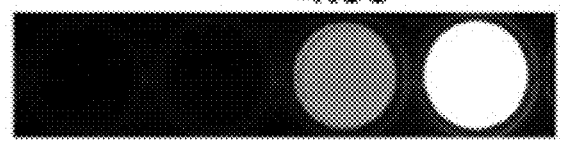
Figure 11:
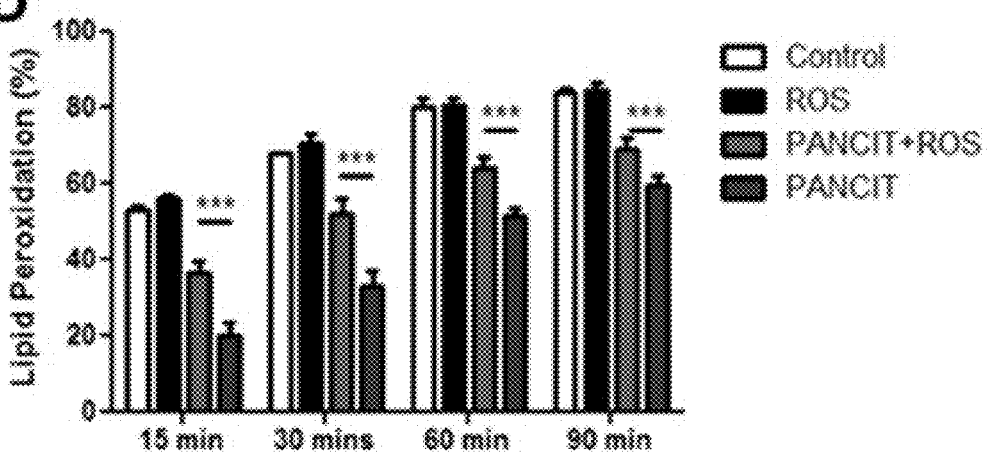

The antioxidant properties of PanCit correlate with its fluorescence signal intensity (FIG. 11C). Furthermore, the optical properties of PanCit may be incorporated into other materials, for example by co-polymerization with 1,8-octanediol or other aliphatic diols to form fluorescent and antioxidant elastomers (FIG. 11B). The fluorescence signal decreases when it is exposed to ROS and loses oxidation protection properties, indicating that fluorescence is useful for monitoring the antioxidant capacity of Pancit. This correlation is highly useful for applications where it is imperative to know when a material's antioxidant capacity is depleted.

Example 6

UV Absorption and Fluorescence Emission is Correlated

UV absorption spectrum of PanCit (50 mg/mL in MQ water) was measured over time during exposure to high intensity UVA radiation using Cary 50 UV/VIS spectrophotometer. Fluorescent intensity of PanCit at 2 mg/mL at identical time points was recorded and quantified using a UVP EpiChemi II bio-imaging darkroom using LabWorks software. PanCit UV absorption sprectrum was compared to commercial photoprotection agents at similar concentrations. Conferral of the fluorescent properties of PanCit to contact lenses was done by imbibition of commercial PHEMA contacts in a 50 mg/mL PanCit solution, triple washing in saline solution and subsequent digital photograph during exposure to UV light source.

Figure 12:
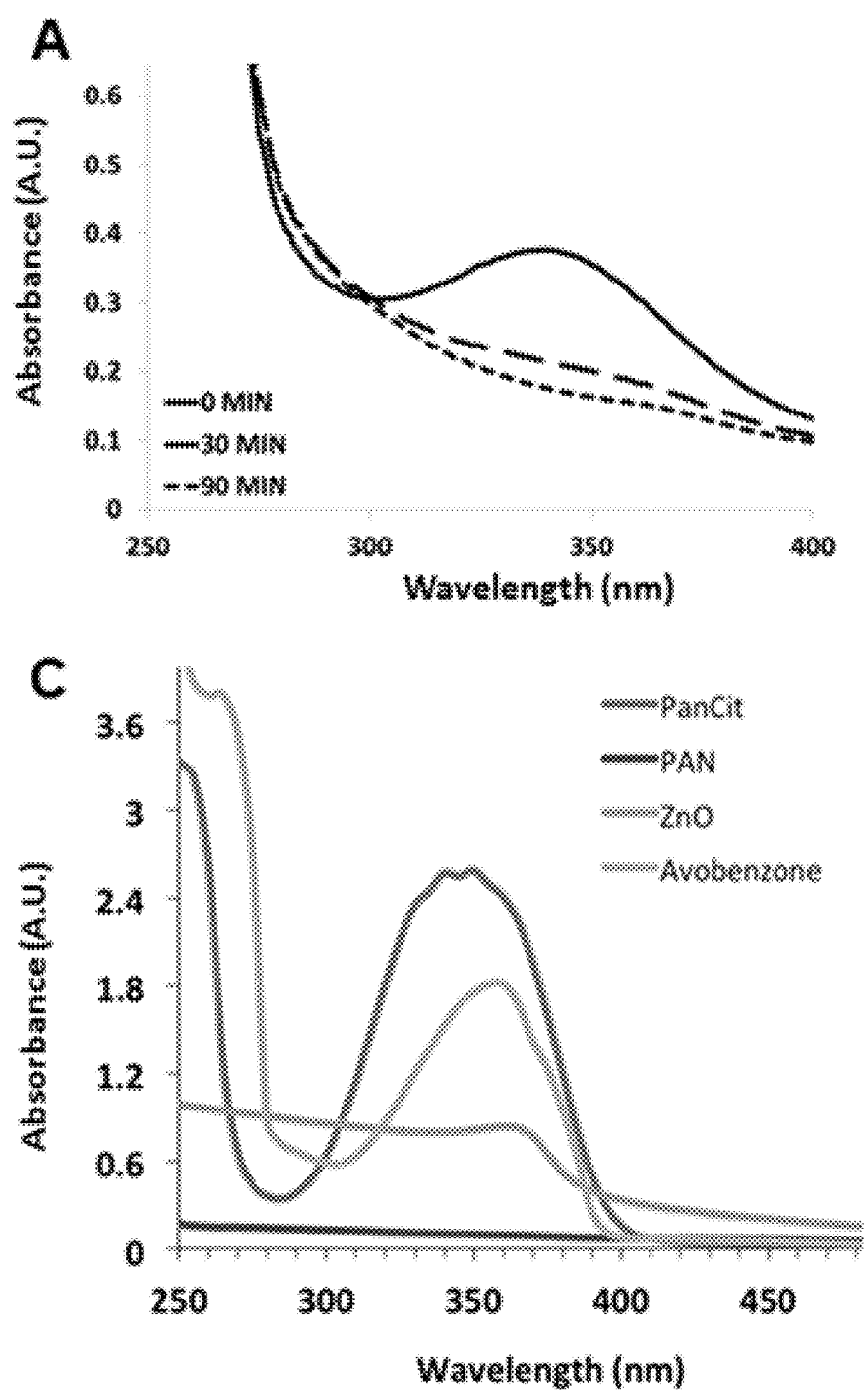
FIGS. 12A-D. PanCit has strong UVA/UVB absorbance that correlates with its fluorescence signal. (A) PANCIT samples exposed to high intensity 365 nm light show reduced UV absorption capacity over time. (B) Fluorescence signal from the same samples also decreases over time due to high intensity 365 nm light. (C) UV-VIS spectra of PanCit and commercial UV absorbers. (D) Fluorescence from pHEMA lens imbibed with PANCIT confirms the feasibility of the proposed experiments.
Figure 12:
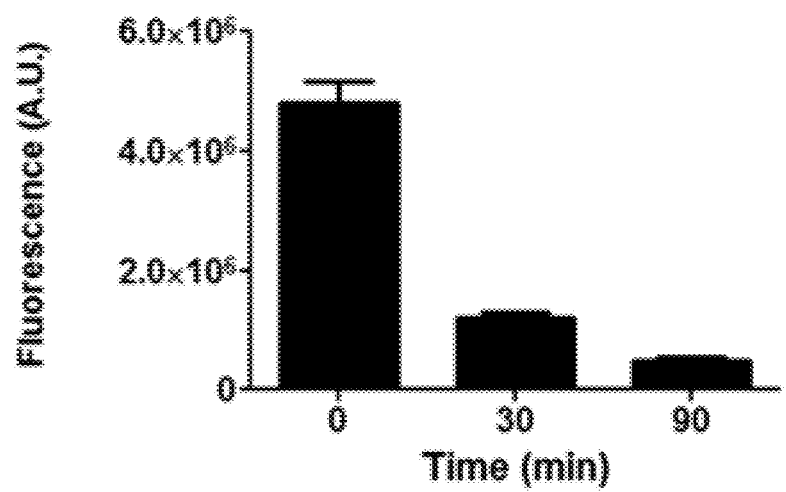
Figure 12:
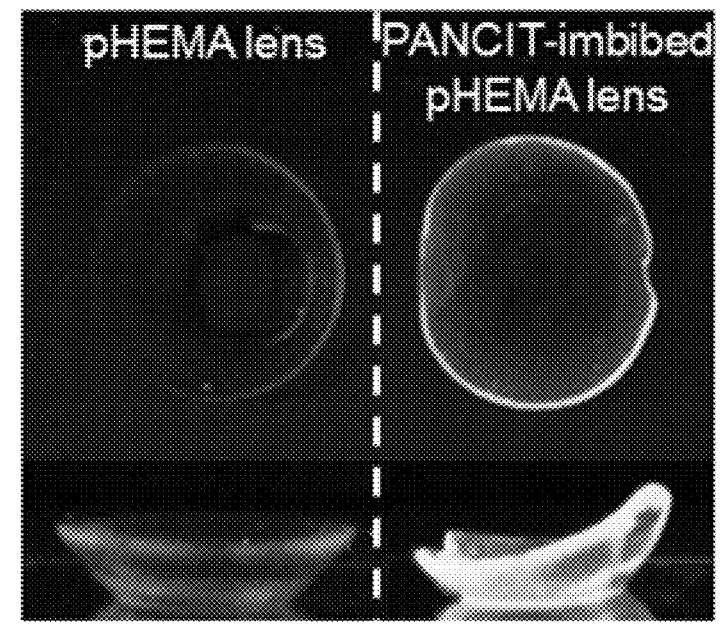

PanCit exhibits high absorbance in the UVA and UVB range and its absorption spectrum is comparable to or better than that of commonly used radiation absorbers found in sunscreens (FIG. 12). When exposed to high intensity UVA radiation, absorbance gradually decreases and the decrease is proportional to its fluorescence signal intensity.

Radiation absorbance, and antioxidant characteristics are used to engineer contact lenses that protect against UVA and UVB radiation damage and oxidative stress challenges that occur on the surface of the eye. The fluorescence characteristic is used to monitor the photo-protective and antioxidant capacity of the lens, creating a functionality assessment method for manufacturers and users.

All publications and patents provided herein are incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

The invention claimed is:

1. A composition comprising panthenol citrate of the formula

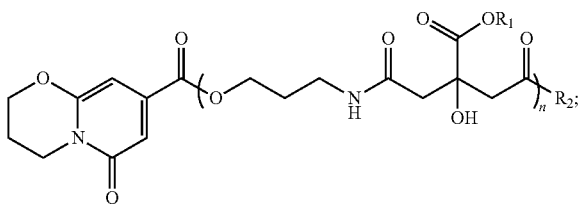

wherein n is 1 to 100; and wherein $R_1$ and $R_2$ are each independently selected from the group consisting of H, pantoic acid, and β-alanol.

2. A composition comprising oligomers of panthenol citrate of the formula

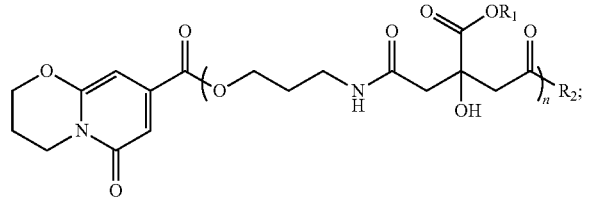

wherein n is 1 to 100; and wherein $R_1$ and $R_2$ are each independently selected from the group consisting of H, pantoic acid, and β-alanol.

3. The composition of claim 1, further comprising one or more additional monomers selected from the group consisting of polyethylene glycol, itaconic acid, glycerol 1,3-diglycerolate diacrylate, N-isopropylacrylamide, glycerol, and a linear aliphatic diol.

4. The composition of claim 1, wherein said composition exhibits photoluminescence and/or antioxidant activity.

5. A composite of the composition of claim 1 and an additional polymeric component.

6. The composite of claim 5, comprising a poly(diol citrate) and/or poly(ε-caprolactone).

7. A composition formulated for topical administration to a human or animal subject comprising the composition of claim 1.

* * * * *